(12) United States Patent
Li

(10) Patent No.: US 8,426,150 B2
(45) Date of Patent: Apr. 23, 2013

(54) PROCESS FOR DIFFERENTIAL POLYPEPTIDES DETECTION AND USES THEREOF

(76) Inventor: Rongxiu Li, Shanghai (CN)

( * ) Notice: Subject to any disclaimer, the term of this patent is extended or adjusted under 35 U.S.C. 154(b) by 353 days.

(21) Appl. No.: 12/784,627

(22) Filed: May 21, 2010

(65) Prior Publication Data

US 2011/0020836 A1 Jan. 27, 2011

Related U.S. Application Data

(60) Provisional application No. 61/180,310, filed on May 21, 2009.

(51) Int. Cl.
*G01N 33/53* (2006.01)
*G01N 31/00* (2006.01)

(52) U.S. Cl.
USPC ........ 435/7.21; 435/7.1; 435/287.9; 436/501; 436/518; 530/300; 530/350

(58) Field of Classification Search .................. None
See application file for complete search history.

(56) References Cited

U.S. PATENT DOCUMENTS 6,670,194 B1 * 12/2003 Aebersold et al. ............ 436/173

* cited by examiner

*Primary Examiner* — Lisa Cook
(74) *Attorney, Agent, or Firm* — Lathrop & Gage LLP; James H. Velema, Esq.; Andrew T. Wilkins

(57) ABSTRACT

Provided herein is an affinity media and the construction and use thereof. The affinity media may be used, for example, for the detection of differential proteins/peptides by depletion of proteins/peptides similar to those in a control sample from a test sample in the search for biologically and pathologically important proteins/peptides. The detected differential proteins/peptides provide vital information for biomarker discovery, drug target discovery, and personalized medicine and treatment.

29 Claims, 4 Drawing Sheets

PROCESS FOR DIFFERENTIAL POLYPEPTIDES DETECTION AND USES THEREOF

RELATED APPLICATION

This application claims priority to U.S. Provisional Application No. 61/180,310, filed May 21, 2009, entitled "PROCESS FOR DIFFERENTIAL POLYPEPTIDES DETECTION AND USES THEREOF." The contents of any patents, patent applications, and references cited throughout this specification are hereby incorporated by reference in their entireties.

FIELD OF THE INVENTION

Provided herein is a process and reagents for detection of differences between polypeptides of a control sample and a test sample and the use of these differential polypeptides in personal medicine, diagnostics and drug discovery.

BACKGROUND OF THE INVENTION

A genome holds the "genetic blueprint" that determines the genotypic make-up of every organism, and its individual susceptibility or resistance to diseases. However, the onset of many common chronic diseases is not predictable and does not follow Mendelian family patterns. Instead, these diseases appear to be caused by a usually unknown number of genes interacting with various environmental factors. A few examples of these diseases include coronary heart disease, hypertension, diabetes, obesity, various cancers, Alzheimer's disease, Parkinson's disease, and others. Even with the same set of genomes, two organisms can develop different functional cells in different organs and tissues, in different stages of development and disease progression. For humans, exercise, diet, social interaction, psychology, and environmental factors (e.g., toxins) all play an important role in making each person have a unique protein portfolio, resulting from the interaction of many genes and his environment. Even in the same person, the expression pattern of a gene in different tissues, organs, or cells may be different due to different time and environmental controls.

Therefore, it is unrealistic to expect that individual variability in disease onset and drug treatment outcomes will be wholly attributable to genetic causes. Personalized medicine must include testing for variations in proteins in addition to genes, gene expression, and metabolites. The test results are correlated with drug response, disease state, prevention, or treatment prognosis, and they help physicians individualize treatment for each patient with greater precision. Since the dynamic nature of protein state reflects a person's real time physiology, choosing the right treatment (the right drug in the right dose) for the right patient at the right time would be more relevant to diagnosis or prognosis, defining disease states, assessing risk profiles and outcomes, and setting up individual therapeutic strategies.

Cancer remains a devastating disease throughout the world. The diagnostic classification of a cancer used to be based on the organ or tissue location where it originated in the body. However, the malignant cells that constitute a tumor are markedly heterogeneous. For example, ~38 leukemia and ~51 lymphoma types have been identified, and cannot be explained only by differences between genomic information. Despite advances in diagnostic technologies, surgical management, and therapeutic modalities, the long-term survival is still poor in most patients suffering from cancer due to the fact that the majority of cancers are detected in their advanced stages and some have distant metastases, rendering treatment ineffective. The detection and the classification of a patient by key protein spectrums inside and/or on the surface of the cell would provide new information on how rapidly the cancer might spread and how it might respond to specific treatments, and also provide possibility for early diagnosis, which would lead to intervention and treatment long before clinical signs and symptoms appearance. Early detection and classification can also help us to understand preclinical molecular events and detect potential patients at risk. Instead of adopting a trial-and-error approach, physicians can now choose the most effective medication with the fewest side effects from the start. Also, new assays can be developed in clinical diagnostics, where all the available assays are designed for consensus biomarkers and can not detect the protein signals of unknown danger.

The detection of characteristics determining key protein spectrums is of vital importance in accelerating the understanding of disease biological processes, which, in turn, facilitate the discovery of new drug targets and diagnostic disease markers. Thus, the identification of phenotype-specific or disease related protein spectrums are becoming increasingly important in biology and medicine.

The current strategy for detection of protein function or disease related protein spectrums involves the comparison of proteomic profiles of contrast samples. The core proteomic analysis technologies for the separation of proteins and/or peptides are one- and two-dimensional gel electrophoresis, and one- or more-dimensional liquid chromatography, coupled almost exclusively with mass spectrometry. A comparison is then made between the protein profiles in different samples. Co-analysis with two dimensional gel electrophoresis of samples coded with different fluorescent dyes, such as Cy2, Cy3, or Cy5, offers higher degree of reproducibility of sample comparison than separation side-by-side or sequential analyses of one sample at a time.

An important improvement is the two dimensional chromatography fractionation of samples, followed by isotope labeling of proteins. A comparison is then made using mass spectrum profiling. The protocols include heavy isotope (e.g., $^{15}N$, $^{13}C$, and $^{18}O$) incorporation and isotope-coded labeling reagents, which are described in WO01/94935; WO03/102220; US20050069961; US20050100956; US2002/0168644; U.S. Pat. No. 6,670,194; WO03/102018; and WO00/11208. A set of other labeling reagents has been used to label a plurality of samples. The protocol of combining them before or after selecting/enriching for labeled molecules and co-assay together for reliable comparison is described in US20050074794.

Another important improvement is the use of a limited number of immuno-affinity methods to remove more than 20 high abundant serum proteins, which indeed improves the detection proteins that are low in abundance (Yocum A K et al., J. Proteome Res. 2005, 4:1722-1731; Schuchard M D et al., Origins 2005, 21:17-23.) However, the task of comprehensive profiling and characterization of all the proteins in a given sample is overwhelming. Through alternate gene splicing and post-translational modifications, approximately 35,000 genes in the human genome could generate about 100,000-500,000 potentially expressed proteins. It is estimated that the complexity of proteomics may be in the range of 30,000-50,000 proteins of a given sample. Environmental, nutritional, and developmental circumstances have direct effects on the dynamics of protein expression, which leads to an even greater molecular complexity and variations between individuals or same individuals at different circumstances.

Hundreds of thousands proteins are present (cells, tissue, serum, etc.). Current technologies lack sensitivity to allow detection of a few different proteins reliably and repeatedly.

As a result, there is a need for more efficient methods to screen, identify and characterize differential proteins between samples.

SUMMARY OF THE INVENTION

Provided herein is a process and reagents for detection of differences between polypeptides of a control sample and a test sample and the use of these differential polypeptides in personal medicine, diagnostics and drug discovery. In one aspect, the invention provides a process for increasing the concentration of at least one protein or polypeptide in a biological test sample, wherein the protein(s) or polypeptide(s) is differentially present in the biological test sample compared to a biological control sample, comprising:

(a) extracting one or more soluble proteins or peptides from the biological control sample, and developing a composition of antigen binding immunoglobulins capable of binding at least one polypeptide in the biological control sample;

(b) immobilizing the immunoglobulins onto a base matrix to prepare an affinity media;

(c) extracting soluble proteins or peptides from the biological test sample; and (d) contacting the soluble proteins from the biological test sample with the affinity media, and collecting a resulting sample, wherein the differential proteins or peptides are enriched in the resulting sample.

In certain aspects, the invention provides a process for increasing the concentration of at least one polypeptide in a biological test sample, wherein the polypeptide(s) is differentially present in the biological test sample compared to a biological control sample, comprising:

(a) extracting one or more soluble proteins or peptides from the biological control sample, and developing a composition of antigen binding immunoglobulins capable of binding at least one polypeptide in the biological control sample;

(b) immobilizing the immunoglobulins onto a base matrix to prepare an affinity media;

(c) extracting the soluble proteins or peptides from a biological test sample; and (d) passing the extracted soluble proteins from the biological test sample through a column packed with the affinity media, collecting the flow-through fraction and concentrating the proteins contained therein, wherein the differential proteins or peptides are enriched in the sample of interest.

In one preferred embodiment, the process further comprises:

(e) characterizing the enriched polypeptide(s) in the biological test sample. In another preferred embodiment, the enriched polypeptide(s) in the process is characterized by mass spectrometry.

In another aspect, this invention provides a process for identifying differential protein(s) or peptide(s) between a biological test sample and a biological control sample, wherein said process comprises:

(a) extracting one or more soluble proteins or peptides from the biological control sample, and immunizing an animal with the proteins or peptides to prepare antigen binding proteins capable of binding the soluble proteins or peptides;

(b) immobilizing the antigen binding proteins onto a base matrix to prepare an affinity media;

(c) extracting soluble proteins or peptides from a biological test sample;

(d) passing extracted soluble proteins from the biological test sample through a column packed with the affinity media, collecting the flow-through fraction and concentrating the proteins contained therein, wherein said differential proteins or peptides are enriched in the sample of interest; and (e) detecting the differential proteins or peptides with mass spectrometry.

In another aspect, this invention provides a process for identifying differential protein(s) or peptide(s) between a biological test sample and a biological control sample, wherein said process comprises:

(a) extracting one or more soluble proteins or peptides from the biological control sample, and immunizing an animal with the proteins or peptides to prepare antigen binding proteins capable of binding the soluble proteins or peptides;

(b) immobilizing the immunoglobulins onto a base matrix to prepare an affinity media;

(c) extracting soluble proteins or peptides from a biological test sample;

(d) mixing the soluble protein extract from the biological test sample with the affinity media, separating and collecting the supernatant fraction and concentrating the proteins contained therein, wherein the differential proteins or peptides are enriched in the sample of interest; and (e) detecting the differential proteins or peptides with mass spectrometry.

In one embodiment, the antigen binding polypeptides in the process are antibodies or antibody fragments, or combinations thereof. In another embodiment, the supernatant in the process is collected from the solid affinity media with centrifugation. In a further embodiment, the supernatant in the process is collected from the solid affinity media with a magnetic field. In still another embodiment, the supernatant in the process is collected from the solid affinity media with suction under vacuum. In yet another embodiment, the supernatant in the process is collected from the solid affinity media with pressure liquid through solid media.

In another aspect, this invention provides a process of identifying at least one polypeptide as a disease marker in a biological test sample from a subject suffering from said disease, wherein said polypeptide(s) is differentially present in the biological test sample compared to a biological control sample from another subject free of said disease, comprising:

(a) extracting soluble polypeptides from said biological control sample;

(b) developing antigen binding polypeptides capable of binding to said extracted soluble polypeptides;

(c) immobilizing said antigen binding polypeptides onto a base matrix to prepare an affinity media;

(d) extracting soluble polypeptides from said biological test sample;

(e) passing extracted soluble proteins in (d) through a column packed with the affinity media and collecting the flow-through fraction, such that the concentration percentage of said polypeptide(s) as the disease marker to the total polypeptides in the biological test sample in said flow-through fraction is increased;

(f) optionally, concentrating said polypeptide(s) in the flow-through fraction; and (g) identifying the polypeptide(s) as the disease marker.

In one preferred embodiment, the identified disease marker from the process can be further used for diagnostic or therapeutic purpose.

In some preferred embodiments, both subjects in the process are humans.

In other preferred embodiments, the biological sample in the process is a biological sample from a patient group, wherein the patient group suffers from one or more diseases selected from the group consisting of arthritis, autoimmune disease, bacterial infection, blood disorder, cancer, cardiovascular disease, diabetes, genetic disorder, inflammation, mental disease, metabolic disorder, neurological disorders, respiratory diseases and viral infection. In one preferred embodiment, the patient suffers from adrenal cancer, bile duct cancer, extrahepatic bile duct cancer, bladder cancer, bone cancer, brain cancer, breast cancer, cervical cancer, colon cancer, colorectal cancer, esophageal cancer, gallbladder cancer, gastric cancer, head & neck cancer, Hodgkin's disease, lymphoma, intestinal cancer, kidney cancer, laryngeal cancer, leukemia, acute lymphocytic leukemia (all), acute myelogenous leukemia (aml), chronic lymphocytic leukemia (cll), liver cancer, lung cancer, also see small cell, non-small cell, lymphoma, b-cell lymphoma, melanoma, mesothelioma, multiple myeloma, oral cancer, ovarian cancer, pancreatic cancer, pharyngeal cancer, prostate cancer, rectal cancer, rectum cancer, skin cancer, stomach cancer, testicular cancer, throat cancer, thyroid cancer, uterine cancer, vaginal cancer, vulvar cancer. In another preferred embodiment, the neurological disorder is Alzheimer's disease, Parkinson's disease, dementia, epilepsy, headache disorders, multiple sclerosis, neuroinfections, stroke and traumatic brain injuries.

In other preferred embodiments, the biological sample used in the process is body fluid selected from the group consisting of ascites, blood, plasma, serum, chyle, semen, interstitial fluid, lymph fluid, menses, breast milk, sweat, tears, urine, vaginal lubrication, Cowper's fluid or pre-ejaculatory fluid, female ejaculate, mucus, pleural fluid, pus, saliva, sebum (skin oil), chyme, and vomit.

In other preferred embodiments, the biological sample used in the process is a patient body tissue selected from aorta, artery, bladder, bone, breast, cervix, colon, esophagus, fungi, kidney, liver, lung, pancreas, placenta, skin, small intestine, spinal cord, spleen, stomach, thyroid, tonsil, or uterus.

In other preferred embodiments, the biological sample used in the process is from mice, rats, pigs, guinea pigs, rabbits, horses, cows, dogs, cats, monkeys or humans.

In other preferred embodiments, the process is used to screen disease biomarkers from plasma.

In other preferred embodiments, the process is used to screen disease biomarkers from pathologic tissue.

In other preferred embodiments, the process is used to assess health risks for individuals.

In other preferred embodiments, the process is used to discover drug targets.

In other preferred embodiments, the process is used to monitor the therapeutic effect of disease treatment.

In other preferred embodiments, the process is used for personalized treatment for diseases.

In other preferred embodiments, the process is used to identify a treatment regimen.

In one preferred embodiment, the putative uncharacterized protein DKFZp686O01196 is identified from the process as a disease marker from liver cancer patients.

In another preferred embodiments, HPX (Hemopexin), Transthyretin or Isoform 1 of Haptoglobin-related protein is identified from the process as a disease marker from myopia patients.

In another aspect, this invention provides a use of the putative uncharacterized protein DKFZp686O01196 as a diagnostic biomarker in plasma of liver cancer patients.

In another aspect, this invention provides a use of one or more protein(s) selected from the group consisting of Hemopexin, Transthyretin and the Isoform 1 of Haptoglobin-related protein as a diagnostic biomarker in plasma of myopia patients.

In other aspects, this invention provides an affinity media comprising antigen binding polypeptides and a supporting matrix. In one preferred embodiment, the antigen binding polypeptides are antibodies or antibody fragments, or a combination thereof. In another preferred embodiment, the antigen binding polypeptides are prepared by immunizing a vertebrate animal with all the proteins in the control sample. In one preferred embodiment, the vertebrate animal is a bird or a mammal. In one preferred embodiment, the bird is selected from a group consisting of dove, chicken, hen, goose, duck, rooster, turkey, ostrich, lesser rhea, penguin, pelican, shoebill, bald ibis, flamingo, swan, buzzard, eagle, awk, kite, vulture, bateleur, kestrel, merlin, crane, bustard, parrot, amazon, owl, hornbill, and toucan. In another embodiment, the mammal is selected from a group consisting of dog, cat, bull, calf, cat, donkey, horse, lamb, sheep, goat, colt, hogs and pigs (swine), gerbils, cattle, cow, oxen, yaks, mules, ass, buffalo, camels, llamas and alpacas, alpaca, guinea pigs, hamsters, rabbits, ferrets, chipmunks and squirrels, gophers and groundhogs, mice and rats, moles, porcupines, beavers, lemming, kangaroo, wallaby, koalas, dormouse, porcupine, hare, shrew, hedgehog, chinchillas, galago, coypu utan, gibbon, pangolin, dolphin, fox, wolf, bear, panda, cheetah, caracal, jaguar, lion, leopard, tiger, seal, walrus, elephant, ass, zebra, tapir, rhinoceros, babirusa, peccary, hippopotamus, guanaco, vicugna, deer, addax, oryx, bontebok, cyprus mouflon, dama gazelle, gaur, goral, lechwe, takin, antelope, lemur, tamarin, monkey, mangabey, baboon, drill, gorilla, baboons, capuchins, galagos, macaques, chimpanzee and human.

In another embodiment, the antigen binding polypeptides are prepared by immunizing an animal with all the proteins from the body fluid of the animal, wherein the body fluid is selected from the group consisting of ascites, blood, plasma, serum, chyle, semen, interstitial fluid, lymph fluid, menses, breast milk, sweat, tears, urine, vaginal lubrication, Cowper's fluid or pre-ejaculatory fluid, female ejaculate, mucus, pleural fluid, pus, saliva, sebum (skin oil), chyme, and vomit.

In another embodiment, antigen binding polypeptides are prepared by immunizing an animal with all the proteins from the body tissue of the animal, wherein the body tissue is selected from the group consisting of aorta, artery, bladder, bone, breast, cervix, colon, esophagus, fungi, kidney, liver, lung, pancreas, placenta, skin, small intestine, spinal cord, spleen, stomach, thyroid, tonsil, and uterus.

In just another embodiment, the antigen binding polypeptides are prepared by immunizing an animal with all the proteins purified from cells originated from the body tissue of the animal, wherein the body tissue is selected from the tissue group consisting of the aorta, artery, bladder, bone, breast, cervix, colon, esophagus, fungi, kidney, liver, lung, pancreas, placenta, skin, small intestine, spinal cord, spleen, stomach, thyroid, tonsil, and uterus.

In another embodiment, the supporting matrix is a compound or material, wherein the material is particulate or non particulate, soluble or insoluble, or porous or nonporous.

In still another embodiment, the supporting matrix comprises agarose, cellulose, hydroxyethylmethacrylate, polyacrylamide, polystyrenedivinylbenzene, hyper D, toyopearl, and glass, silica, metal oxide, perfluorocarbons, streamline, magnetic bead, magnetic cortex, filters, filter paper, filter fibric, or walls of capillary tube, or a combination thereof, optionally coated with an organic polymer.

In yet another embodiment, the antigen binding polypeptides are attached to the supporting matrix through activation and immobilization through amine reactive chemistry, sulfhydryl reactive chemistry, carbonyl chemistry, hydroxyl reactive chemistry, active hydrogen reactive chemistry, or photoreactive reactive chemistry. In one preferred embodiment, the sulfhydryl reactive chemistry utilizes cyanogen bromide, carbonyl diimidazole, divinylsulfone, azlactone, cyanuric chloride, 2-fluoro-1-methylpyridinium toluene-4-sulfonate, tosyl chloride, tresyl chloride, iodoacetyl, bromoacetyl, maleimide, pyridyl disulfide, epoxyl, bisoxirane, or 5-thio-2-nitro benzoic acid as a reactant. In another preferred embodiment, the carbonyl chemistry utilizes hydrazide or reductive animation. In another preferred embodiment, the hydroxyl reactive chemistry utilizes cyanogen bromide, cyanuric chloride, epoxyl, or bisoxirane. In another preferred embodiment, the active hydrogen reactive chemistry utilizes a Diazonium or a Mannich Condensation. In another embodiment, the photoreactive reactive chemistry utilizes p-azidophenyl glyoxal, azidobenzoyl hydrazide, sulfosuccunimidyl-6-(4'-azido-2'-nitrophenylamino)hexanoate, or N-[4-(p-azidosalicylamido)butyl]-3'-(2'-pyridyldithio) propionamide.

In another aspect, provided herein is an affinity media that can be used to practice the methods described herein. Thus, in one embodiment, provided herein is an affinity media comprising a base matrix and antigen binding immunoglobulins capable of binding at least one polypeptide in a biological control sample, wherein the immunoglobulins are developed from one or more soluble proteins or peptides that were extracted from the biological control sample, wherein the affinity media can be used for purposes for obtaining or increasing the concentration of at least one protein or peptide in a biological test sample, wherein the protein or peptide is differentially present in the biological test sample compared to the biological control sample.

DETAILED DESCRIPTION OF THE INVENTION

Figure 1:
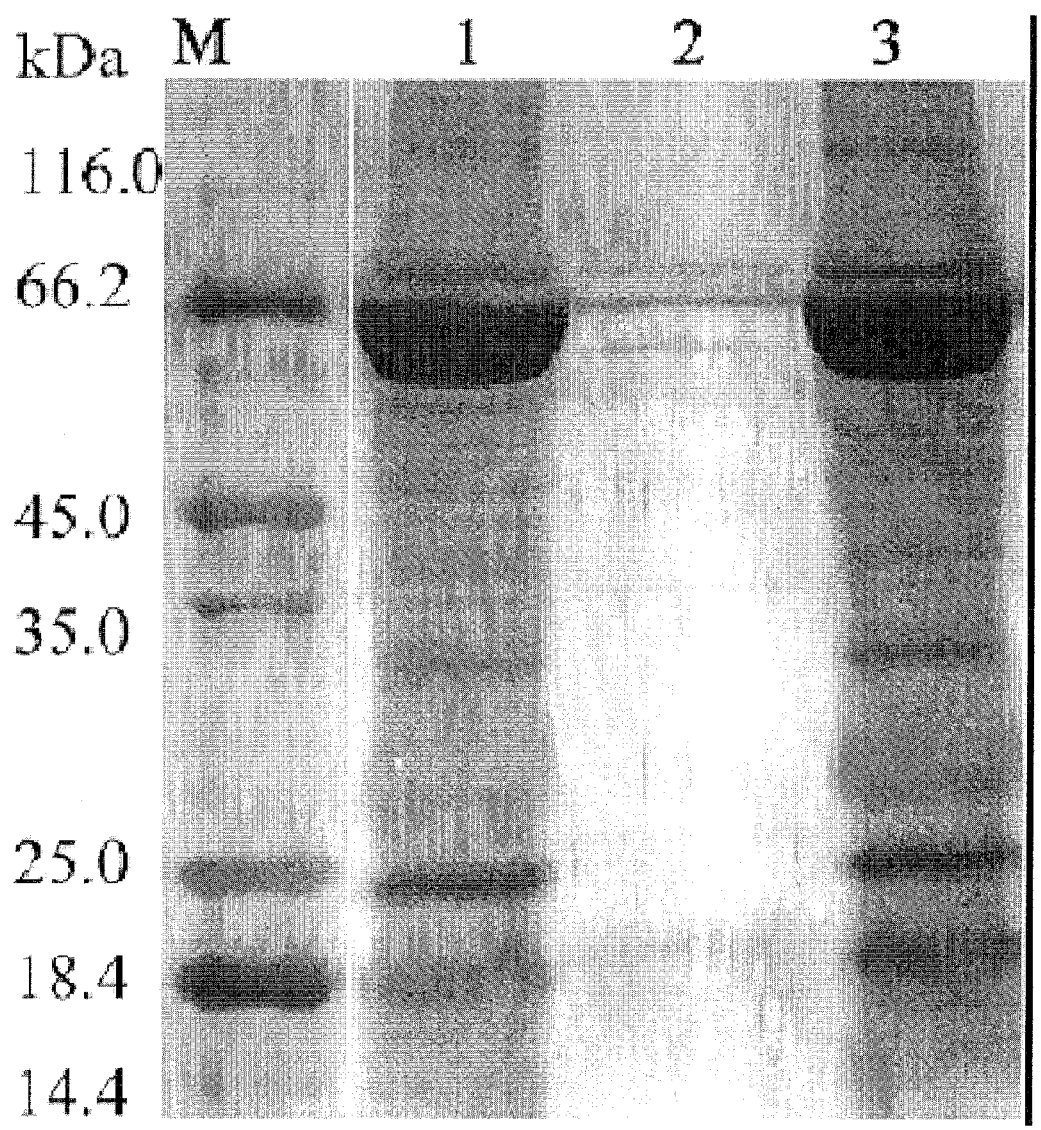
FIG. 1 depicts the SDS-PAGE analysis for the detection of differential polypeptides in plasma from a healthy volunteer. Lanes from left to right are: protein markers, original sample, differential fraction and depletion fraction.
Figure 2:
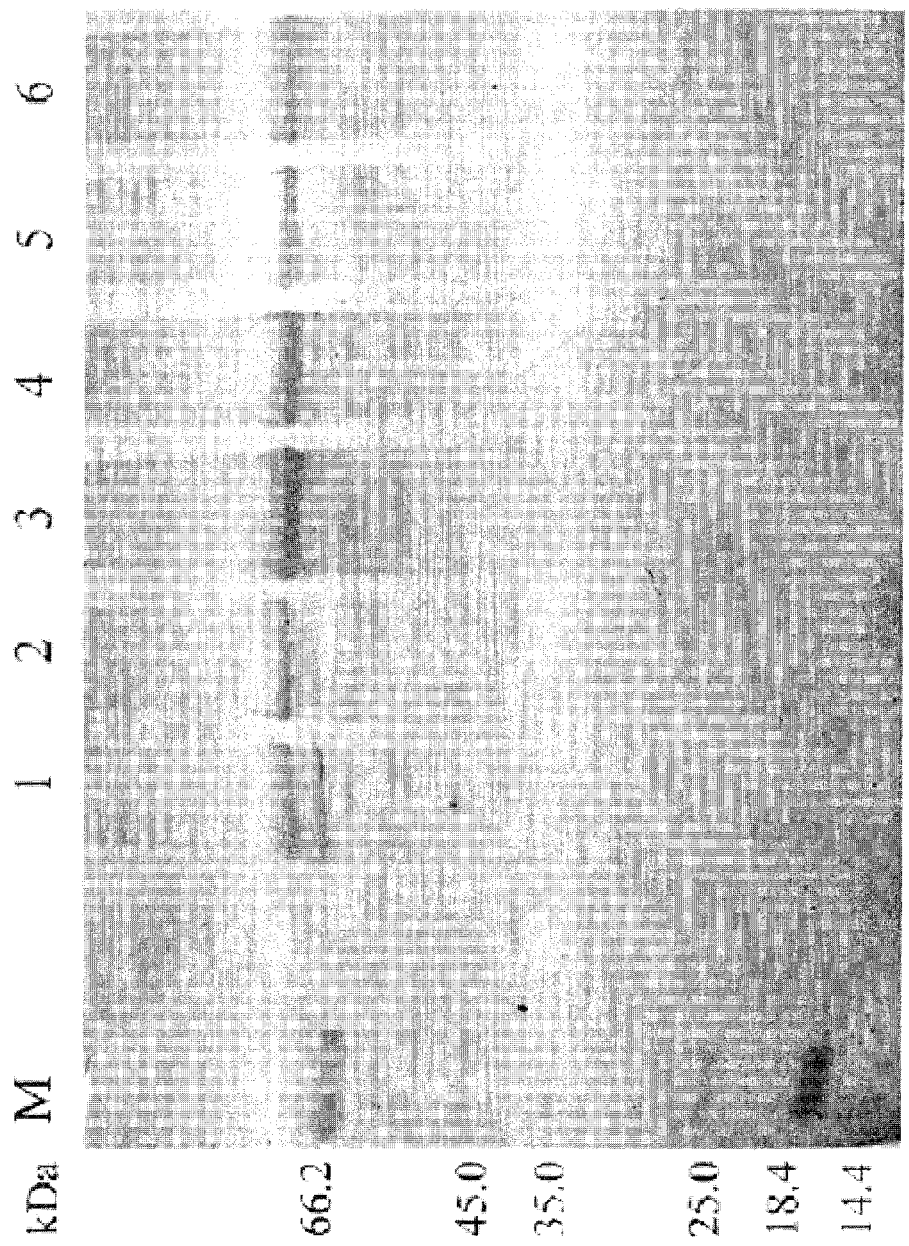
FIG. 2 depicts the SDS-PAGE analysis for the detection of differential polypeptides of plasma from liver cancer patients. Lanes from left to right are: Lane M: protein markers; Lane 1: differential fraction of a healthy volunteer; Lanes 2-6: differential fraction of liver cancer patients.
Figure 3:
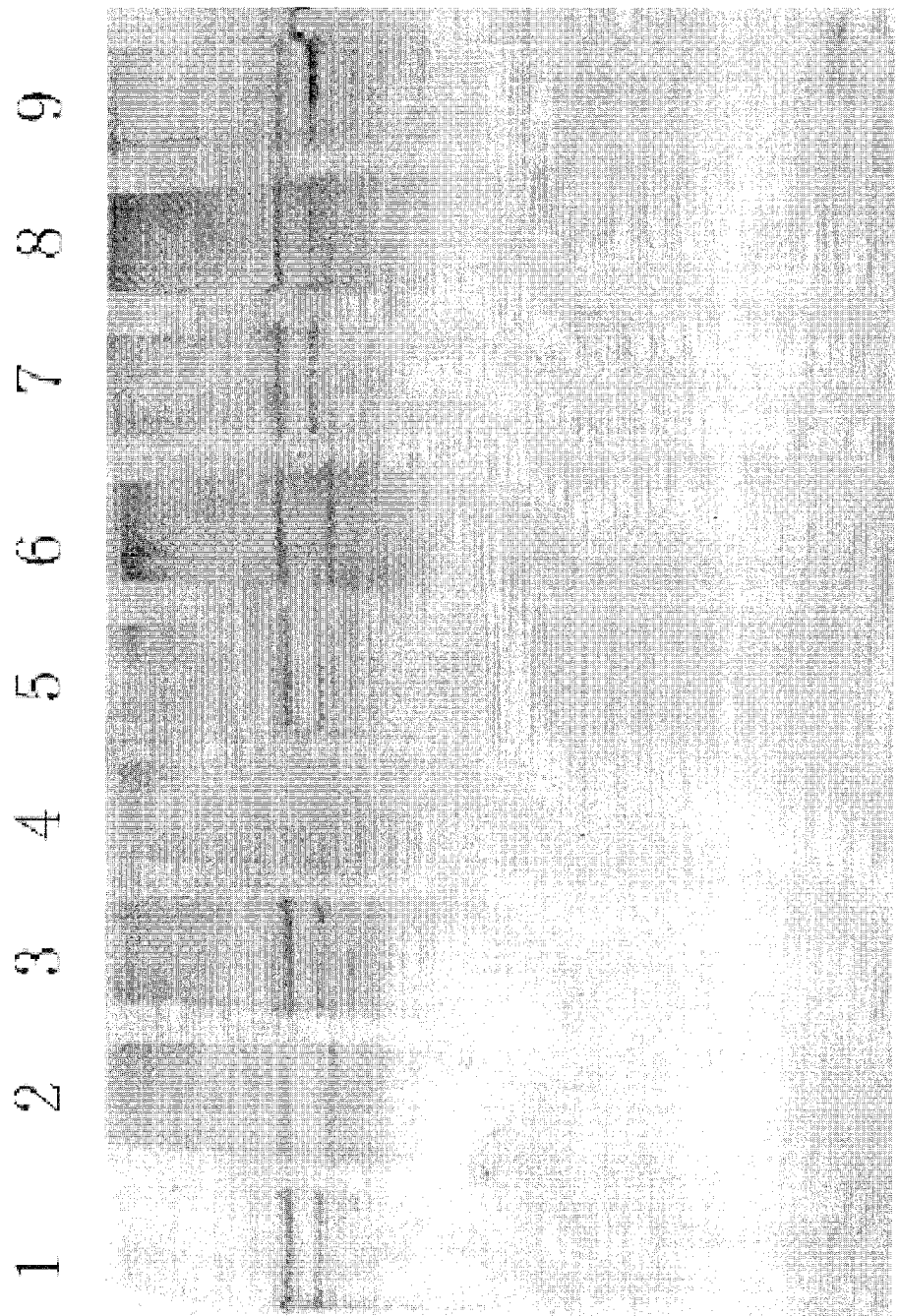
FIG. 3 depicts the SDS-PAGE analysis for the detection of differential polypeptides of plasma from deep myopia patients. Lanes from left to right are: Lanes 1-9: differential fraction of deep myopia patients.
Figure 4:
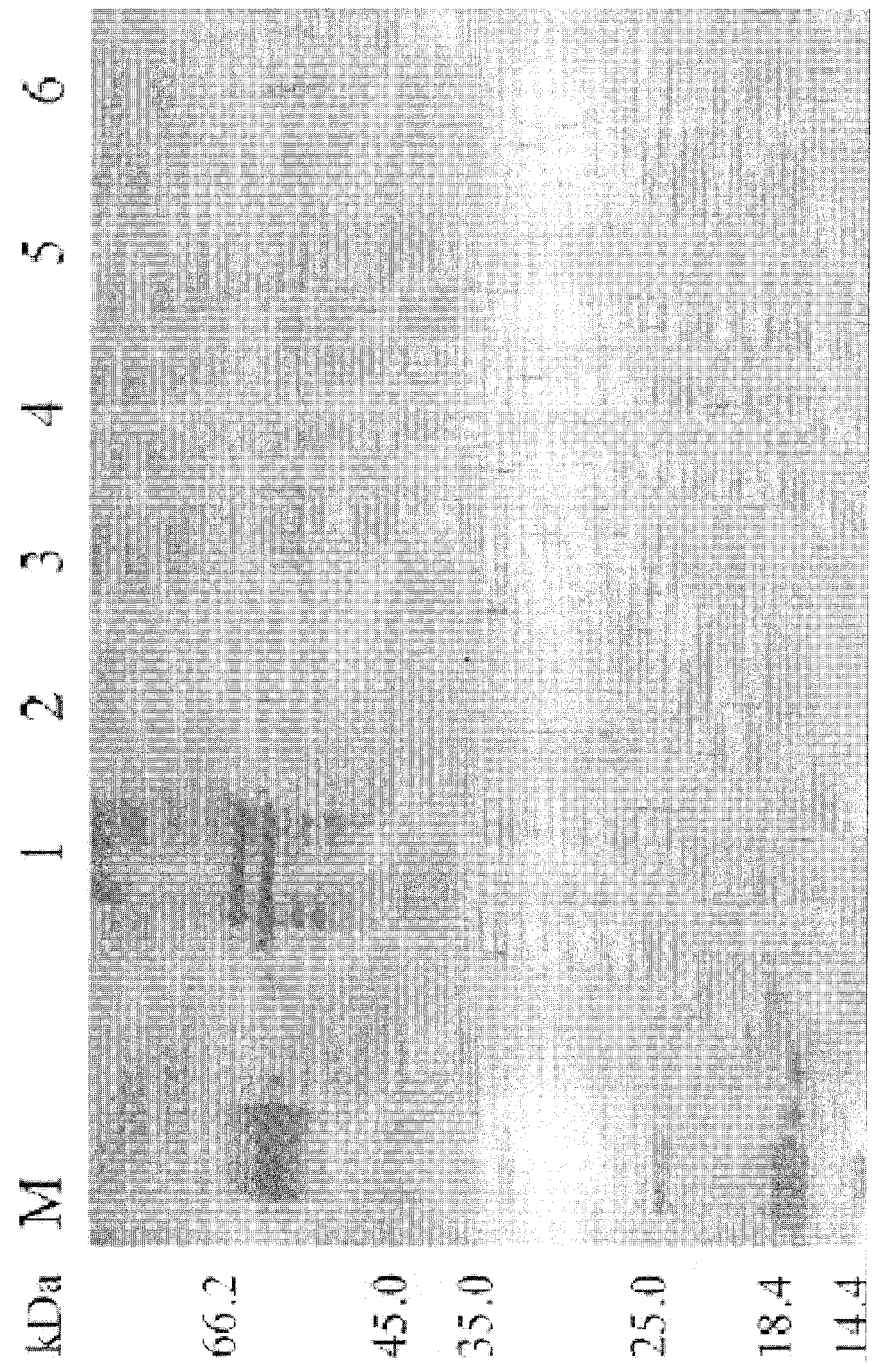
FIG. 4 depicts the SDS-PAGE analysis for the detection of differential polypeptides of plasma from healthy pregnant female volunteers. Lanes from left to right are: Lane M: protein markers; Lane 1: differential fraction of a healthy volunteer; Lanes 2-6: differential fraction of healthy pregnant female volunteers.

The separation and characterization of proteins between samples of abnormal and normal subjects is an area of importance, especially with regard to the identification of disease biomarkers and drug targets. Such information is relevant to the diagnosis of a disease at the biochemical level, clinical studies following the treatment effects of different drug therapies, and the discrimination between the responses of different patients to the same medical treatment. For personalized medicine, the above test results are correlated with drug responses and disease states to help an individualized prevention or treatment. Thus, methods for detecting and characterizing protein difference and/or differential proteins are of great interest to the pharmaceutical and health care industries.

Since the abnormal physiological and/or pathological conditions in a subject are usually developed from normal/healthy physiological conditions, the majority of proteins in the samples of a subject are the same as those in a normal subject. The protein difference and/or differential proteins between the two samples are usually few. The same proteins in both normal and abnormal samples are large in number, and mostly high in abundance. The large number of high abundant proteins, mostly normal proteins with physiological functions (house-keeping proteins), pose an obstacle for detecting and characterizing protein/polypeptide difference and/or differential proteins/polypeptides. The most frequently used strategies incorporate the use of one- and two-dimensional gel electrophoresis, one- and higher-dimensional liquid chromatography, and mass spectrometry to profile all the proteins in a test sample of interest and in a control sample separately. Then, the protein profiles are compared to recognize and identify the differences. However, these techniques are limited by their separation resolution, analysis capacity of protein numbers, the detection range between high and low abundance of existing proteins, and the masking effects of high level of background noises formed by large number of house-keeping proteins.

The most effective method for improvement is the use of antibodies (e.g., 6, 20 or 60) specific to high abundant serum proteins to remove the high abundant serum proteins to detect low abundance proteins in human serum. This approach removes the masking effects of some high abundance proteins over low abundance proteins, but has minimal effect on the complexity caused by a large number of house-keeping proteins or other common proteins between control and test samples.

The process of differential protein detection provided herein relies on the design of an affinity media binding all the proteins in samples. Such affinity media has the affinity to interact specifically with all proteins in a control sample. When a test sample is mixed with such affinity media in a solid form, the proteins of the same kind as in the control sample will bind to the affinity media and get absorbed and removed from the test sample, leaving only different kinds of proteins not existing in the control sample. These proteins left in the test sample are the differential proteins and can be easily detected and characterized with mass spectrometry, or other protein analysis and identification tools. This approach eliminates the masking effect of the high level background noises, formed by the proteins existing in the control sample, and reduces the workload of protein analysis and identification such as with mass spectrum analysis, making it a promising technique for detection and characterization of differential polypeptides. When done in a reverse mode, this method can also be used to identify polypeptides expressed only in the control sample but not in the test sample.

In order that the present invention may be more readily understood, certain terms are first defined. Additional terms are set forth throughout the detailed description.

The term "sample" includes the term "biological sample", "pathological sample", "proteins of sample", "proteins existing in sample", and "proteins in sample", and refers to protein lysates, protein extracts, ascites, blood, plasma, serum, urine, lymph, interstitial fluid, amniotic fluid, aqueous humour, cerumen (e.g., earwax), Cowper's fluid, chyme, breast milk, feces, mucus (e.g., nasal drainage and phlegm), pleural fluid, pus, saliva, sebum (e.g., skin oil), semen, sweat, tears, vaginal secretion, vomit, any biological sample, or any proteinacious sample.

The term "control sample" refers to a sample of a biological or physiological state as a starting state to change. In a preferred embodiment of the invention, control sample is plasma from healthy human.

As used herein, the term "test sample" refers to a sample of a biological state, a physiological state, and/or a disease, which is differentiated, pathologically progressed, and/or transformed from another biological or physiological state of a starting point. Usually, "test sample" is related to a specific biological function, a physiological state, and or a disease. In a preferred embodiment of the invention, test samples are plasma from liver cancer patients, deep myopia patients, or a pregnant female. In another preferred embodiment of the invention, test samples are tissue samples from cancer patients. In another particular embodiment of the invention, test samples may be surgery tissue and pathological samples from cancer patients. In a further embodiment of the invention, test samples may be cardiovascular surgery tissue and pathological samples.

In a preferred embodiment of the invention, proteins or polypeptides of a sample are plasma proteins or polypeptides in the sample, which is free of blood cells.

As used herein, the term "protein" and "polypeptide" refer to a polymer of two or more of the natural amino acids or non-natural amino acids.

The term "low abundance proteins" includes proteins present at a low concentration in a protein sample of interest. For example, the concentration of the low abundance protein of interest may be less than 50% of the total protein concentration in the sample. Also, for example, the concentration of the low abundance protein of interest may be less than 50%, 40%, 30%, 25%, 20%, 15%, 10%, 5%, 1%, 0.1%, 0.01%, 0.001%, 0.0001%, 0.00001%, 0.000001%, or 0.0000001% of the total protein concentration in the sample.

In contrast, the term "high abundance proteins" includes proteins present at a high concentration in a protein sample of interest. For example, the concentration of the high abundance protein(s) of interest may be greater than 50%, 40%, 30%, 25%, 20%, 15%, 10%, 5%, 1%, 0.1%, 0.01%, 0.001%, 0.0001%, 0.00001%, 0.000001%, or 0.0000001% of the total protein concentration in the sample.

The term "matrix" includes the term "support matrix." In one embodiment, the matrix is a solid supporting matrix. In a preferred embodiment of the invention, matrix is optionally activated agarose.

There exists a considerable number of activating agents for attaching ligands to support matrices (e.g., sepharose). The procedures by which such activating and immobilization steps are carried out are well known to those skilled in the art. In a preferred embodiment of the invention, the matrix is with CNBr activated agarose beads.

As used herein, the term "affinity media" refers to matrix media immobilized with antibody or antibodies having the ability to bind/associate with polypeptides in the sample solution.

The term "antibody" refers to whole antibodies and any antigen-binding fragment (i.e., "antigen-binding portion," "antigen-binding polypeptide," or "immunobinder") or single chain thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody fragment" includes scFv antibodies, F(ab')2 fragments, Fab fragments, Fd fragments, Fv fragments, and single domain antibody fragments (DAbs).

The term "protein subtraction" refers to the process of using affinity media prepared with the immobilization of antibodies against proteins of a control sample, which has the ability to bind/associate proteins present/existing in the control sample and can be used to remove similar proteins/polypeptides from a test sample, leaving only "differential proteins"/"different proteins"/"proteins of difference" in the test sample solution.

The term "differential proteins" includes "different proteins", "proteins of difference" and refers to proteins present or existing in one sample (test sample) and not present or existing in the other sample (control sample).

The term "subject" is known in the art, and, as used herein, refers to a warm-blooded animal, more preferably a mammal, including, e.g., non-human animals such as rats, mice, rabbits, cats, dogs, sheep, horses, cattle, in addition to humans. In a preferred embodiment, the subject is a human. The subjects can be those susceptible to treatment with a soluble antigen-binding polypeptides of the present invention.

The term "disease" is known in the art, and, as used herein, includes, e.g., cancers, cardiovascular disorders, heart diseases, neurological disorders, an autoimmune disorder, an infectious disease, a genetic disease, a behavioral disorder, or a mental disorder.

The term "cancer" is known in the art, and, as used herein, includes, e.g., a generic term for a large group of diseases that can affect any part of the body, with the feature of rapid creation of abnormal cells that grow beyond their usual boundaries, invasion adjoining parts of the body, and spreading to other organs. The cancer may be a carcinoma or a sarcoma, including brain cancers, lung cancer, breast cancers, stomach cancers, liver cancers, pancreatic cancers, bladder cancers, cervical cancers, colon cancers, prostate cancers, colorectal cancers, or skin cancer (e.g., melanoma), esophagus cancers, lymphoma and leukemia.

The term "neurological disorder" is known in the art, and, as used herein, refers to diseases of the central and peripheral nervous system, including, e.g., the brain, spinal cord, cranial nerves, peripheral nerves, nerve roots, autonomic nervous system, neuromuscular junction, and muscles. These disorders include, e.g., epilepsy, Alzheimer's disease and other dementias, cerebrovascular diseases including stroke, migraine and other headache disorders, multiple sclerosis, Parkinson's disease, neuroinfections, brain tumors, traumatic disorders of the nervous system such as brain trauma, and neurological disorders as a result of malnutrition.

The term "cardiovascular disorder" is known in the art, and, as used herein, refers to a cardiovascular disease or cardiovascular diseases that technically refer to any disease that affects the cardiovascular system and/or involves the heart or blood vessels (arteries and veins), including, e.g., those related to atherosclerosis (arterial disease), coronary heart diseases (heart attacks), cerebrovascular diseases, raised blood pressure (hypertension), peripheral artery disease, rheumatic heart disease, congenital heart disease and heart failure, deep vein thrombosis and pulmonary embolism.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, delay, relieve, alter, remedy, ameliorate, improve or affect the disease, the symptoms of disease or the predisposition toward disease.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "patient" includes human and other mammalian subjects that receive either prophylactic or therapeutic treatment.

In one embodiment, the invention pertains, at least in part, to a method of preparation of antibody or antibody fragments against proteins of a control sample, followed by immobilization of prepared antibody or antibody fragments on a matrix to prepare immune-affinity media. In one preferred embodiment, a biological test sample is treated with a prepared immune-affinity media capable of binding to polypeptides in the control sample and is removed of polypeptides existing in both the test sample and the control sample, thus resulting in an increase of concentration of at least one polypeptide differentially presents in the test sample but not in the control sample.

In certain embodiments, the polypeptides in plasma samples of liver cancer patients but not in healthy persons as control are prepared by passing said plasma samples from patients through an affinity column containing immobilized antibody or antibody fragments against plasma proteins of healthy persons, while the polypeptides of normal function bind to the antibody or antibody fragments on the column and are removed from the patient's plasma sample and the flow-through fraction contains plasma polypeptides specific to liver cancer patients.

In another embodiment, this invention also pertains to a method of depleting polypeptides from a mixture. The method comprises contacting a polypeptide mixture to form a polypeptide complex onto the affinity media, and then removing the polypeptide complexes, such that said polypeptides are depleted from the mixture.

The present invention also provides a method for the subtraction of polypeptides or the depletion of polypeptides of a control sample from a test sample. In one preferred embodiment, the present invention also provides a method for the isolation of functional or pathological state related polypeptides from a proteinacious sample of interest. In a further embodiment, the present invention provides a method for the identification of a change in protein expressions, e.g., a protein in a diseased state was not present and/or expressed in very low abundance in a normal sample, a protein in a normal sample was not present and/or expressed in very low abundance in diseased state.

In a preferred embodiment, the proteins isolated by the methods of the present invention can be used as drug targets of the disease for drug discovery. In another preferred embodiment, the leftover proteins by the methods of the present invention can be used as diagnostic agents to identify a subject with a disease or a diseased sample. In another embodiment, proteins left over by the methods of the present invention can be used as indicator of pathological state for choosing most suitable therapeutic treatment for a subject with a disease. In another embodiment, the leftover proteins by the methods of the present invention can be used as a monitoring tool for following and assessment of the therapeutic effect of a chosen treatment of a subject with a disease or a diseased sample.

The present invention, in part, relates to a novel affinity media preparation on a matrix which may consist of solid, semi-solid, particulate or colloidal materials, or soluble polymers. In one embodiment the novel affinity media is not specialized. The invention further relates to said novel affinity media and the preparation and uses thereof in the proteomic research and diagnostics for differential proteins/peptides and/or the depletion of house-keeping proteins/peptides and/or the depletion of proteins/peptides same as present/existing in control sample.

The present invention further relates to an affinity chromatographic media, the preparation and the use of the chromatographic media in the enrichment of differential proteins/peptides and/or the depletion of house-keeping proteins/peptides and/or the depletion of proteins/peptides same as present/existing in control sample in the field of proteomics of biological samples.

The current invention is based on the notion that most polypeptides present/existing in a control sample can stimulate immune response in experimental animals, such as mouse, rat, and rabbit, and to produce antibodies against these proteins. The immobilization of said antibodies enables them to recognize and bind polypeptides immunologically similar to those polypeptides used for preparation of the antibodies. When a test sample is mixed with the immobilized antibodies, the same proteins used for preparation of the antibodies would be absorbed onto the said immobilized antibodies and removed, the proteins not bound to the said immobilized antibodies will remain in the test sample solution for further mass spectrum characterization. These proteins will contain the differential proteins not present in control sample.

The affinity media of the present invention comprise a solid, usually permeable, support matrix, to which the antibodies are covalently attached. The affinity media can be packed in a chromatographic column, or a permeable membrane filter, or any similar devices known to a person with skills in the art. Target proteins in the sample are bound and delayed in the support matrix under near physiological conditions when the sample is passed over. The proteins unbound in the flow-through fraction can be concentrated and characterized.

A feature of the present invention is the provision of a general tool for the enrichment (i.e., increasing the abundance of a protein) of differential proteins and the subtraction/depletion (i.e., removal and/or decreasing the abundance of a protein) of proteins in the field of proteomics. The affinity media with antibodies or antibody fragments against the control sample provided herein have the ability to interact with the same proteins in test sample. By way of example, a group of proteins the same as in the control sample can be bound onto affinity media, with proteins of the test sample different from those in the control sample left in the flow-through fraction.

The invention will now be described in further detail with reference to the following examples. The examples are provided for illustrative purposes, and are not to be construed as limiting the scope of the invention in any way.

EXAMPLES

Throughout the examples, the following materials and methods were used unless otherwise stated.
Materials and Methods In general, the practice of the present invention employs, unless otherwise indicated, conventional techniques of chemistry, molecular biology, recombinant DNA technology, immunology (especially, e.g., antibody technology), and standard techniques of polypeptide preparation. See, e.g., Sambrook, Fritsch and Maniatis, Molecular Cloning Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds., Ausubel et al., John Wiley & Sons (1992).

Example 1

Preparation of Affinity Media

Two days before first immunization and each boost injection, 0.5 ml blood was collected from the central ear artery of New Zealand white rabbits with a 21-gauge needle and allowed to clot and retract at 37° C. overnight. The serum was decanted and clarified by centrifugation at 2,500 rpm for 15 minutes, then stored at −40° C. for later ELISA testing. Healthy human plasma (1 ml, ~50 mg/ml) and 1.0 ml complete Freund's adjuvant were mixed thoroughly to form a stable emulsion. Then the emulsion was injected at multi-points beneath the skin of three 8-week-old rabbits (subcutaneously) in the area around the shoulders. Boosts were carried out in 2-week interval by immunizations with healthy human plasma (1 ml, ~50 mg/ml) emulsified in 1 ml incomplete Freund's adjuvant. The ELISA was used to monitor the production of antibodies. After the $3^{rd}$ boost immunization, when the titer reached $10^5$, the rabbits were bled via carotid. Blood was collected with sodium citrate as anticoagulants. Plasma was then collected by centrifugation at 1,000 rpm at 4° C. for 10 minutes to remove red blood cells, and stored at −70° C.

ELISA: healthy human plasma were diluted to protein concentration of 100 ng/100 µl in coating buffer (50 mmol/L bicarbonate buffer, pH 9.6), and then transferred to Polystyrene 96-well microtiter plates (100 µl per well) and incubated at 4° C. overnight. The plates were washed five times with PBST (0.02 M phosphate, 0.15 M NaCl, 0.15% Tween-20, pH 7.4) with 5 minutes standing before discarding the washing PBST, added with 200 µl of defatted milk (protein concentration: 2%) in PBST and incubated for 2 hours at 37° C. to block free binding sites in wells. Then plates were washed five times with PBST (0.02 M phosphate, 0.15M NaCl, 0.15% Tween-20, pH 7.4) with 5 minutes standing before discarding the washing PBST. Rabbit serum was diluted to 1/100, 1/1,000, 1/10,000, 1/100,000, 1/1,000,000 with defatted milk (protein concentration: 2%) in PBST, transferred in 100 µl aliquot to each well of the plate, and incubated for 1 hour at 37° C., followed by washing five times with PBST (0.02 M phosphate, 0.15 M NaCl, 0.15% Tween-20, pH 7.4) with 5 minutes standing before discarding the washing PBST. Goat anti-rabbit IgG-horseradish peroxidase conjugate (1:10,000 diluted) was added in 1000 aliquot, incubated for 1 hour at 37° C. and washed five times with PBST (0.02 M phosphate, 0.15 M NaCl, 0.15% Tween-20, pH 7.4) with 5 minutes standing before discarding the washing PBST. Finally, 100 µl aliquot of substrate solution (10 ml substrate solution containing 4 mg Ortho-Phenylenediamine (OPD), 0.0074 g sodium citrate, 0.0184 g $Na_2HPO_4.12H_2O$, and 15 µl of 30% $H_2O_2$ (hydrogen peroxide), pH 4.8) was added and incubated for 30 minutes at 37° C. The reaction was stopped by adding 50 µl of 2 mol/L $H_2SO4$. Absorbance of each well in the plates was measured at 492 nm on a microplate reader and plotted against dilution to find the titer (dilution times) when the reading at 492 nm was halved.

Rabbit antibody purification: 10 ml Rabbit plasma was diluted by 5 fold with PBS (0.02 M phosphate, 0.15 M NaCl, pH 7.2), and 10 ml was loaded onto Protein G-sepharose column (1 m) pre-equilibrated with PBS. The column was washed with PBS until 280 nm absorbance was leveled off at base line, and then eluted with Gly-HCl buffer (0.2 M, pH 2.5). The peak fraction was collected. The purification was repeated 5 times until all the rabbit plasma was finished. The elution fraction was pooled and the protein concentration was estimated, by measuring absorbance at 280 nm and 260 nm, to be 35 mg. The antibody quality was analyzed by reducing SDS-PAGE, while the heavy chain and light chain of antibodies were in total more than 95% by gray density scan and integration.

Affinity media preparation: Sepharose CL 4B was washed with 500 ml dd$H_2O$. Forty-five milliliters of settled bed Sepharose resin were transferred into a 250 ml glass beaker, resuspended in 100 ml dd$H_2O$ pre-cooled to 4° C., and stirred with large magnetic stir bar in an ice bucket so that ice surrounds the sides of the beaker. Forty-two grams of cyanogen bromide were dissolved in 50 ml acetonitrile, and pooled into the beaker with sepharose under stirring. Under pH monitoring, NaOH (20% w/v) was added to maintain the pH around 10.5-11.5 (pH did not drop bellow 10 for 10-15 minutes). Then the cyanogen bromide-activated Sepharose was transferred into a scintered glass funnel, washed with 1 liter of 4° C. dd$H_2O$ under a modest vacuum, and then mixed with purified rabbit antibody in 0.1 M $NaHCO_3$ (pH 8.5) at 4° C. for 35 hours. The immobilization was stopped by addition of 0.5 ml of ethanolamine, and mixed at 4° C. for 5 hours. The prepared immobilized rabbit antibody affinity media was washed with 400 ml 0.01 M phosphate buffer (pH 7.0) and stored at 4° C. until use.

Example 2

Detection of Differential Polypeptides of Plasma from Healthy Volunteers

Differential polypeptides preparation: 20 µl human plasma of healthy volunteers was diluted with 980 µl Phosphate buffer (10 mM, pH 7.0). The total protein amount was estimated to be about 1 mg, from its absorbance at 280 nm and 260 nm and the equation of $C(mg/ml)=1.45 \times A_{280nm} - 0.74 \times A_{260nm}$. The diluted plasma was loaded onto the affinity column (1 ml) with immobilized affinity media in Example 1. The flow-through was collected and concentrated to 20 µl, in which 5 µl was analyzed with reducing SDS-PAGE (12%) and stained with silver stain protocol. It was shown that there were only 9 faint bands visible, and the elution fraction has similar band pattern to the original sample. The reducing SDS-PAGE (12%) analysis confirmed the effectiveness of removal of most of the proteins of normal function in healthy human plasma.

Differential Polypeptides Identification and Characterization:

For Trypsin digestion, the following buffers were prepared:

Digestion Buffer: 30 mg of ammonium bicarbonate was dissolved in 15 ml ultrapure water.

Reducing Buffer: 200 µl of TCEP was diluted in 2 ml digestion buffer.

Alkylation Buffer: 60 mg of iodoacetamide (IAA) was dissolved in 3 ml digestion buffer.

Activated Trypsin Solution: 20 µl of Trypsin Storage Solution was added to 20 µg of lyophilized modified Trypsin. The solution was further added with 180 µl of ultrapure water. 1.8 ml digestion Buffer was then added to the diluted Trypsin to make 2 ml for the total volume.

Twenty-five micrograms of modified Trypsin were dissolved in 2.5 ml Tosylphenylalanylchloromethane (TCPK), mixed with 250 µl 0.1% redistilled acetonitrile. Fifteen microliters of the above Trypsin solution were activated in 100 µl 50 mM NH$_4$HCO$_3$. Five microliters of the above flow-through proteins were reduced with 100 µl of Reducing Buffer (200 µl TCEP in 2 ml Digestion buffer) and incubated at 60° C. for 10 minutes. One hundred microliters of alkylation buffer (60 mg iodoacetamide (IAA) in 3 ml digestion buffer) were added to the tube and the mixture was incubated in the dark at room temperature for 1 hour. Then 20 µl activated Trypsin solution was added to the tube and incubated at 37° C. for 1 hour and continuously incubated at 25° C. overnight with gentle mixing.

The peptides mixture was then loaded onto a Zorbax 300 SB-C18 peptide traps (Agilent Technologies, Wilmington, Del.) to desalt. The separation was performed on a Zorbax 300SB-C18 reverse phase capillary column (150 µm inner diameter×15 cm, Agilent Technologies) at 250 nl/min with a linear gradient of 4-50% B over 50 min (A: 0.1% formic acid; B: 84% CH$_3$CN and 0.1% formic acid), a step up to 100% B in 4 min, and then holding at 100% B for 10 minutes. The peak was online injected into a Finnigan LTQ (single linear quadrupole ion trap) mass spectrometer for peptide identification.

Mass spectrometry was carried out on a Finnigan LTQ linear ion trap. The MS method consisted of a cycle combining one full MS scan with ten MS/MS events (25% collision energy). Dynamic exclusion duration was set to 30 seconds. The MS/MS spectra from all the runs were searched using BOWORKS protein identification software against database of ipi HUMAN v3.36. The SEQUEST filter was set to when Charge +1, Xcorr≧1.9; Charge +2, Xcorr≧2.2; Charge +3, Xcorr≧3.75; and DelCN≧0.1. As a confirmation of the effectiveness of the process of differential polypeptides preparation, another healthy human plasma sample was tested, with the result of 37 proteins/peptides detected and listed in Table 1. These include some leftover of high abundant plasma proteins of normal function, such as albumin, immunoglobulin, transferrin, Fibrinogen, complement C3. The other 31 proteins/peptides belong to low abundant proteins of total abundance <1%, including proteins/peptides of dermcidin (DCD), cystatin-A, CSH1;CSH2 Isoform 1 of Somatotropin, growth hormone, alpha-2-macroglobulin. Some proteins with biological functions inside cells were detected as well, including protein tyrosine phosphatase, RNA polymerase II elongation factor, UBB ubiquitin and ribosomal protein S27, Isoform 2 of zinc finger protein 57 homolog, Isoform 2 of Titin, Isoform 1 of Nicastrin, Isoform 2 of Armadillo repeat-containing protein 3, Isoform 3 of cAMP-specific 3',5'-cyclic phosphodiesterase 4A, adenosine monophosphate deaminase 2, signal recognition particle 54 kDa protein etc. Although the plasma sample was collected from healthy person, among the detected proteins/peptides, chromosome 1 open reading frame 113 and DKFZp686D0972 hypothetical protein LOC345651 are hypothetical proteins whose function to be explored. Nicastrin is a transmembrane glycoprotein serving as an essential component of the gamma-secretase complex, physically associating with presenilin and playing an important role in stabilization and correct localization of presenilin to the membrane bound gamma-secretase complex. Nicastrin also serves as a docking site for gamma-secretase substrates, such as APP and Notch, by directly binding to them and presenting them properly to gamma-secretase to ensure the correct cleavage process. The existence of Nicastrin in plasma may suggest a possible link with Alzheimer's disease (AD). The detection of BRIP1 Isoform 1 of Fanconi anemia group J protein in plasma suggests a possible relevance with Fanconi anemia (FA), an autosomal recessive disease marked by bone marrow failure, birth defects, and cancer. The detection of disease related proteins in plasma provides a good starting point to establish biomarker for early diagnostics.

In Table 1, the polypeptides detected in plasma from three healthy volunteers and its initial classification and comments are shown.

TABLE 1

| Group | Proteins detected |
|---|---|
| | Healthy volunteer 1 |
| Proteins of interests | Gene_Symbol = BRIP1 Isoform 1 of Fanconi anemia group J protein |
| | Gene_Symbol = NCSTN Isoform 1 of Nicastrin precursor |
| | Gene_Symbol = RP5-1054A22.3 Novel protein |
| | Gene_Symbol =- Chromosome 1 open reading frame 113 |
| | Gene_Symbol = DKFZp686D0972 hypothetical protein LOC345651 |
| Plasma proteins | Gene_Symbol = ALB Uncharacterized protein ALB |
| | Gene_Symbol = IGHG1 Putative uncharacterized protein DKFZp686N02209 |
| | Gene_Symbol = IGHM FLJ00385 protein (Fragment) |
| | Gene_Symbol = IGHG2 Putative uncharacterized protein DKFZp686I04196 (Fragment) |
| | Gene_Symbol = TF Serotransferrin precursor |

TABLE 1-continued

| Group | Proteins detected |
|---|---|
| Cell proteins | Gene_Symbol = FGA Isoform 1 of Fibrinogen alpha chain precursor<br>Gene_Symbol = FGG Isoform Gamma-B of Fibrinogen gamma chain precursor<br>Gene_Symbol = FGB Fibrinogen beta chain precursor<br>Gene_Symbol = LOC653879 similar to Complement C3 precursor<br>Gene_Symbol = A2M Alpha-2-macroglobulin precursor<br>Gene_Symbol = IGKV1-5 IGKV1-5 protein<br>Gene_Symbol = DCD Dermcidin precursor<br>Gene_Symbol = CSTA Cystatin-A<br>Gene_Symbol = GH1; CSH1; CSH2 Isoform 1 of Somatotropin precursor<br>Gene_Symbol = PTPRK Protein tyrosine phosphatase, receptor type, K<br>Gene_Symbol = ELL RNA polymerase II elongation factor ELL<br>Gene_Symbol = RPS27A; UBC; UBB ubiquitin and ribosomal protein S27a precursor<br>Gene_Symbol = ZFP57 Isoform 2 of Zinc finger protein 57 homolog<br>Gene_Symbol = TTN Isoform 2 of Titin<br>Gene_Symbol =- 42 kDa protein<br>Gene_Symbol = ARMC3 Isoform 2 of Armadillo repeat-containing protein 3<br>Gene_Symbol = PDE4A Isoform 3 of cAMP-specific 3',5'-cyclic phosphodiesterase 4A<br>Gene_Symbol = AMPD2 Adenosine monophosphate deaminase 2<br>Gene_Symbol = DIO2 Type II iodothyronine deiodinase<br>Gene_Symbol = MYH11 Myosin-11<br>Gene_Symbol = SRP54 Signal recognition particle 54 kDa protein<br>Gene_Symbol = KIAA0372 Tetratricopeptide repeat protein 37<br>Gene_Symbol =- Lamin-like protein in HindIII repetitive element derived DNA, 3' end (Fragment)<br>Gene_Symbol = SLC22A11 Isoform 1 of Solute carrier family 22 member 11<br>Gene_Symbol = ZCCHC11 Isoform 1 of Zinc finger CCHC domain-containing protein 11<br>Gene_Symbol = GRHL1 Uncharacterized protein GRHL1<br>Gene_Symbol = B3GALT6 B3GALT6 protein (Fragment) |
| | Healthy volunteer 2 |
| Proteins of interests Cell proteins | Gene_Symbol = RP5-1054A22.3 Novel protein<br>Gene_Symbol =- Conserved hypothetical protein<br>Gene_Symbol = UCHL1 Ubiquitin carboxyl-terminal hydrolase isozyme L1<br>Gene_Symbol = LOC100093698 Similar to Ataxin 3 isoform 3<br>Gene_Symbol =- 42 kDa protein<br>Gene_Symbol = PREPL prolyl endopeptidase-like isoform C<br>Gene_Symbol = LOC728378 Chimeric POTE-actin protein<br>Gene_Symbol = PDE4A Isoform 3 of cAMP-specific 3',5'-cyclic phosphodiesterase 4A<br>Gene_Symbol = BRIP1 Isoform 1 of Fanconi anemia group J protein<br>Gene_Symbol = MNT Max-binding protein MNT<br>Gene_Symbol = CSPP1 Isoform 1 of Centrosome and spindle pole-associated protein 1<br>Gene_Symbol = NF1 Isoform 2 of Neurofibromin<br>Gene_Symbol = HNRPDL Isoform 1 of Heterogeneous nuclear ribonucleoprotein D-like<br>Gene_Symbol = CNTN4 Isoform 1 of Contactin-4 precursor<br>Gene_Symbol = MTHFD1 C-1-tetrahydrofolate synthase, cytoplasmic<br>Gene_Symbol = C6orf204 Isoform 1 of Coiled-coil domain-containing protein C6orf204<br>Gene_Symbol = MYH11 Myosin-11<br>Gene_Symbol = GALNT5 Polypeptide N-acetylgalactosaminyltransferase 5<br>Gene_Symbol =- CDNA FLJ43087 fis, clone BRTHA3019105<br>Gene_Symbol = CXCL6 Line-1 reverse transcriptase<br>Gene_Symbol = GYG2 Isoform Alpha of Glycogenin-2<br>Gene_Symbol = GRIN2C N-methyl-D-aspartate receptor 2C subunit precursor<br>Gene_Symbol = PAK2 similar to p21-activated kinase 2<br>Gene_Symbol = PPM1J Isoform 1 of Protein phosphatase 1J<br>Gene_Symbol = TTN Isoform 2 of Titin<br>Gene_Symbol = AKAP10 Mitochondrial A kinase PPKA anchor protein 10<br>Gene_Symbol = CRIM1 Cysteine-rich motor neuron 1 protein precursor<br>Gene_Symbol = B3GALT6 B3GALT6 protein (Fragment) |
| Plasma proteins | Gene_Symbol = TF Serotransferrin precursor<br>Gene_Symbol = ALB Uncharacterized protein ALB<br>Gene_Symbol = IGHG2 Putative uncharacterized protein DKFZp686I04196<br>Gene_Symbol = IGL@ IGL@ protein<br>Gene_Symbol = IGHA1 IGHA1 protein |

TABLE 1-continued

| Group | Proteins detected |
|---|---|
| | Healthy volunteer 3 |
| Proteins of interests | Gene_Symbol = LOC731914 hypothetical protein |
| Cell proteins | Gene_Symbol = ILF2 Interleukin enhancer-binding factor 2
Gene_Symbol = PIK3C2A Phosphatidylinositol-4-phosphate 3-kinase C2 domain-containing alpha polypeptide
Gene_Symbol = JUP Junction plakoglobin
Gene_Symbol = TTN Isoform 2 of Titin
Gene_Symbol = C6orf204 Isoform 1 of Coiled-coil domain-containing protein C6orf204
Gene_Symbol = MYH11 Myosin-11
Gene_Symbol = BMP3 Bone morphogenetic protein 3 precursor
Gene_Symbol = UCHL1 Ubiquitin carboxyl-terminal hydrolase isozyme L1
Gene_Symbol = GSN Isoform 1 of Gelsolin precursor
Gene_Symbol = LMOD1 Leiomodin 1
Gene_Symbol = SLCO5A1 Solute carrier organic anion transporter family member 5A1
Gene_Symbol = SEC23A Protein transport protein Sec23A
Gene_Symbol =- 42 kDa protein |
| Plasma proteins | Gene_Symbol = TF Serotransferrin precursor
Gene_Symbol = ALB Uncharacterized protein ALB
Gene_Symbol = IGHG2 Putative uncharacterized protein DKFZp686I04196
Gene_Symbol = IGHA1 IGHA1 protein |

Example 3

Detection of Differential Polypeptides of Plasma from Liver Cancer Patients

Liver cancer related differential plasma polypeptides preparation: 20 µl plasma from liver cancer patients was diluted with 980 µl Phosphate buffer (10 mM, pH 7.0). Total protein were adjusted to around 1 mg. The diluted plasma was loaded onto the affinity column (1 ml, affinity media prepared in the Example 1), the flow-through was collected and concentrated to 20 µl Five microliters were analyzed with Reducing SDS-PAGE (12%) and stained with silver stain protocol. It was shown that there were few faint bands visible, confirming the successful removal of most of the proteins of normal function in healthy human plasma and the preparation of liver cancer related Differential plasma polypeptides.

Five microliters of the above liver cancer related differential plasma polypeptides samples were reduced with 100 µl of reducing buffer and incubated at 60° C. for 10 minutes, then alkylated by adding 100 µl of alkylation buffer and incubated in the dark at room temperature for 1 hour. It were then digested with addition of 20 µl activated Trypsin solution, incubated at 37° C. for 1 hour and continuously incubated at 25° C. overnight with gentle mixing.

The trypsin digested peptides mixture samples were desalted on a Zorbax 300 SB-C18 peptide traps (Agilent Technologies, Wilmington, Del.) to desalt, and separation was performed on a Zorbax 300SB-C18 reverse phase capillary column (150 µm inner diameter×15 cm, Agilent Technologies) at 250 nl/min with a linear gradient of 4-50% B over 50 minutes (A: 0.1% formic acid; B: 84% $CH_3CN$ and 0.1% formic acid), a step up to 100% B in 4 min, and then holding at 100% B for 10 min. The peak was online injected into a Finnigan LTQ (single linear quadrupole ion trap) mass spectrometer for peptide identification.

Mass spectrometry was carried out on a Finnigan LTQ linear ion trap. The MS method consisted of a cycle combining one full MS scan with ten MS/MS events (25% collision energy). Dynamic exclusion duration was set to 30 seconds.

The MS/MS spectra from all the runs were searched using BOWORKS protein identification software against database of ipi HUMAN v3.36. The SEQUEST filter was set to when Charge +1, Xcorr≧1.9; Charge +2, Xcorr≧2.2; Charge +3, Xcorr≧3.75 and DelCN≧0.1.

17 and 19 polypeptides were detected in two liver cancer patients and listed in Table 2 and Table 3. In addition to the leftover of normal proteins/peptides in plasma such as albumin, immunoglobulin, transferrin, Fibrinogen, or complement C3, there are a few proteins relevant to liver cancer.

Apolipoprotein E: This protein combines with fats (lipids) in the body to form molecules called lipoproteins. Lipoproteins are responsible for packaging cholesterols and other fats and carrying them through the bloodstream. Apolipoprotein E is a major component of a specific type of lipoprotein called very low-density lipoproteins (VLDLs). VLDLs remove excess cholesterols from the blood and carry them to the liver for processing. Maintaining normal levels of cholesterol is essential for the prevention of disorders that affect the heart and blood vessels (cardiovascular diseases), including heart attack and stroke.

It is apparent that fragments of immunoglobulin are frequently detected, which may contain links to cancer. A putative uncharacterized protein DKFZp686O01196 (Gene_Symbol=IGHG1) was detected in both plasma samples of the liver cancer patients. The cDNA was originally cloned from esophagus tumor tissue, and submitted (JAN-2005) to the EMBL/GenBank/DDBJ databases. Another 45 kDa protein (ENSP00000382824; protein model: ENSP00000382824: KERATIN TYPE II CYTOSKELETAL CYTOKERATIN CK KERATIN) belongs to cytokertain family. Its abundance in normal plasma is very low, and the presence of different keratins in either plasma or serum of cancer patients has been recognized for many years and used as tumour markers in the diagnosis of cancer.

In the plasma samples of one liver cancer patients, one 31 kDa protein (KRT13, cytokertain 13) was detected. The detection of cytokeratins in the plasma samples of liver cancer patients was in good agreement with the publication of cytokeratins as markers of differentiation alcoholic liver disease, in epithelia and epithelial tumors.

Apolipoprotein E (Apo E) was detected in the plasma samples of one liver cancer patient as well. It is an indicator of liver function. Its plasma level increased in human hepatocellular carcinoma, in differentially hepatocellular carcinoma chronic viral hepatitis C. It was not detected in healthy volunteers.

The detection of liver cancer related proteins in plasma provides idea starting point to establish biomarker for early diagnostics.

In Table 2, the detected polypeptides and the initial classifications and comments of 3 liver cancer patients are shown.

TABLE 2

| Group | Proteins detected |
|---|---|
| Liver cancer patient 1 | |
| Cancer relevant proteins | Gene_Symbol = APOE Apolipoprotein E precursor |
| | Gene_Symbol =- 45 kDa protein |
| | Gene_Symbol = IGHG1 Putative uncharacterized protein DKFZp686O01196 |
| Normal Plasma proteins | Gene_Symbol = ALB Uncharacterized protein ALB |
| | Gene_Symbol = TF Serotransferrin precursor |
| | Gene_Symbol = LOC653879 similar to Complement C3 precursor |
| | Gene_Symbol = IGHG2 Putative uncharacterized protein DKFZp686I04196 (Fragment) |
| | Gene_Symbol = IGHM FLJ00385 protein (Fragment) |
| | Gene_Symbol = IGKV1-5 IGKV1-5 protein |
| | Gene_Symbol = IGKV1-5 IGKV1-5 protein |
| | Gene_Symbol = IGHM IGHM protein |
| | Gene_Symbol = IGHG1 IGHG1 protein |
| | Gene_Symbol = IGL@ IGL@ protein |
| | Gene_Symbol = IGL@ IGL@ protein |
| | Gene_Symbol = IGL@ IGL@ protein |
| | Gene_Symbol = DCD Dermcidin precursor |
| | Gene_Symbol = CSTA Cystatin-A |
| Liver cancer patient 2 | |
| Cancer relevant proteins | Gene_Symbol = IGHG1 Putative uncharacterized protein DKFZp686O01196 |
| | Gene_Symbol = KRT13 31 kDa protein |
| | Gene_Symbol =- 45 kDa protein |
| Normal Plasma proteins | Gene_Symbol = ALB Uncharacterized protein ALB |
| | Gene_Symbol = LOC653879 similar to Complement C3 precursor |
| | Gene_Symbol = IGHG2 Putative uncharacterized protein DKFZp686I04196 (Fragment) |
| | Gene_Symbol = IGHG1 Putative uncharacterized protein DKFZp686P15220 |
| | Gene_Symbol = IGHM FLJ00385 protein (Fragment) |
| | Gene_Symbol = IGKV1-5 IGKV1-5 protein |
| | Gene_Symbol = IGKV1-5 IGKV1-5 protein |
| | Gene_Symbol = IGHM IGHM protein |
| | Gene_Symbol = IGHG1 IGHG1 protein |
| | Gene_Symbol = IGKC IGKC protein |
| | Gene_Symbol = IGL@ IGL@ protein |
| | Gene_Symbol = IGL@ IGL@ protein |
| | Gene_Symbol = IGKV3-20 Ig kappa chain V-III region HAH precursor |
| | Gene_Symbol = A2M Alpha-2-macroglobulin precursor |
| | Gene_Symbol = CFB Isoform 1 of Complement factor B precursor (Fragment) |
| | Gene_Symbol =- 42 kDa protein |

Example 4

Detection of Differential Polypeptides of Plasma from Deep Myopia Patients

Differential polypeptides preparation: 20 µl plasma collected from deep myopia patients were diluted with 980 µl Phosphate buffer (10 mM, pH 7.0) to a total protein about 1 mg. The diluted plasma was loaded onto the affinity column (1 ml) with immobilized affinity media of Example 1, the flow-through was collected and concentrated to 20 µl, 5 µl was analyzed with Reducing SDS-PAGE (12%) and stained with silver stain protocol. It was shown that there were few faint bands visible, confirmed the effectiveness of removal of most of the proteins of normal function in healthy human plasma.

Five microliters of the above flow-through proteins were reduced with 100 µl of reducing buffer (200 µl of TCEP in 2 ml Digestion buffer) and incubated at 60° C. for 10 minutes. One hundred microliters of alkylation Buffer (60 mg of iodoacetamide (IAA) in 3 ml Digestion buffer) were added to the tube and incubated in the dark at room temperature for 1 hour. Then add 20 µl activated Trypsin solution to the tube, incubated at 37° C. for 1 hour and continuously incubated at 25° C. overnight with gentle mixing.

Then the peptides mixture was injected onto a Zorbax 300 SB-C18 peptide traps (Agilent Technologies, Wilmington, Del.) to desalt. The separation was performed on a Zorbax 300SB-C18 reverse phase capillary column (150 µm inner diameter×15 cm, Agilent Technologies) at 250 nl/min with a linear gradient of 4-50% B over 50 min (A: 0.1% formic acid; B: 84% CH3CN and 0.1% formic acid), a step up to 100% B in 4 min, and then holding at 100% B for 10 min. The peak was online injected into a Finnigan LTQ (single linear quadrupole ion trap) mass spectrometer for peptide identification.

Mass spectrometry was carried out on a Finnigan LTQ linear ion trap. The MS method consisted of a cycle combining one full MS scan with ten MS/MS events (25% collision energy). Dynamic exclusion duration was set to 30 seconds. The MS/MS spectra from all the runs were searched using BOWORKS protein identification software against database of ipi HUMAN v3.36. The SEQUEST filter was set to when Charge +1, Xcorr≧1.9; Charge +2, Xcorr≧2.2; Charge +3, Xcorr≧3.75; and DelCN≧0.1.

Plasmas collected from 8 deep myopia patients were tested. Seven to twenty-nine differential proteins/peptides were detected. The leftover of normal plasma proteins/peptides includes albumin, immunoglobulin, transferrin, Fibrinogen, HBB hemoglobin subunit beta, and platelet basic protein etc. There also exist some proteins with biological functions inside cell as well.

There are some deep myopia related proteins detected. APOB (Apolipoprotein B-100) belongs to plasma protein family. However it was not detected in healthy volunteers. It is reported that the APOB is relevant to the progression of age related macular degeneration (AMD), a leading cause of blindness in industrialized countries and a cause with rising incidence in China. AMD is a complex disease caused by the combination of environmental factors and genetic predisposition. The detection of APOB in plasma of deep myopia patients provides a novel angle for deep myopia research.

Transthyretin (TTR) is detected in plasma of deep myopia patients as well, capable of carrying retinol by binding to retinol-binding protein (RBP). The normal blood level of Transthyretin is 25 to 30 mg/L, while it was not detected in healthy volunteers in this experiment.

It is reported that familial amyloid polyneuropathy (FAP) associated with mutations in the transthyretin (TTR) gene is the most common form of hereditary amyloidosis. Detection of Transthyretin in plasma of deep myopia patients would provide another clue to elucidate the incidents process of deep myopia progression.

The detection of Haptoglobin in plasma of deep myopia patients may provide relevance to oxidative stress of free hemoglobin. Haptoglobin (abbreviated as Hp) is a protein in the blood plasma that binds free hemoglobin released from erythrocytes with high affinity and thereby inhibits its oxidative activity. The haptoglobin-hemoglobin complex will then be removed by the reticuloendothelial system (mostly the spleen). In clinical settings, the haptoglobin assay is used to screen for and monitor intravascular hemolytic anemia.

Haptoglobin phenotyping can be used to predict the risk of diabetic vascular disease. With the haptoglobin test for vascular risk, the drug development would dramatically improve the clinical management of diabetes and cardiovascular disease, ultimately helping the development of personalized therapy.

Hemoglobin or haemoglobin is the iron-containing oxygen-transport metalloprotein in the red blood cell of the blood in mammals and other animals. Its existence in plasma of deep myopia patients may point to the indiscriminative oxidation effect caused by free hemoglobin in plasma.

Hemopexin (HPX) is the plasma protein with the highest binding affinity to heme among known proteins. It belongs to acute phase reactants and is mainly expressed in liver, the synthesis of which is induced after inflammation. Heme is potentially highly toxic because of its ability to intercalate into lipid membranes and to produce hydroxyl radicals.

The detection of Hemopexin (HPX) of in plasma of deep myopia patients may confirm the indiscriminative oxidation effect in the progression of myopia.

The detection of the disease related proteins in plasma provides a good starting point to establish biomarker for early diagnostics, and personalized treatment.

In Table 3, differential proteins/peptides of plasma detected from deep myopia patients, initial classification and comments are shown.

TABLE 3

| Group | Proteins detected |
|---|---|
| Deep myopia patient 1 | |
| Deep myopia relevant proteins | Gene_Symbol = HPX Hemopexin precursor |
| | Gene_Symbol = TTR Transthyretin precursor |
| | Gene_Symbol = APOB Apolipoprotein B-100 precursor |
| Plasma proteins | Gene_Symbol = TF Serotransferrin precursor |
| | Gene_Symbol = ALB Uncharacterized protein ALB |
| | Gene_Symbol = A2M Alpha-2-macroglobulin precursor |
| | Gene_Symbol = IGHM FLJ00385 protein (Fragment) |
| | Gene_Symbol = IGHG1 Putative uncharacterized protein DKFZp686N02209 |
| | Gene_Symbol = IGL@ IGL@ protein |
| | Gene_Symbol = IGHA1 IGHA1 protein |
| | Gene_Symbol = IGKC IGKC protein |
| | Gene_Symbol = CSTA Cystatin-A |
| | Gene_Symbol = PPBP Platelet basic protein precursor |
| | Gene_Symbol =- Anti-(ED-B) scFV (Fragment) |
| Deep myopia patient 2 | |
| Deep myopia relevant proteins | Gene_Symbol = HPX Hemopexin precursor |
| | Gene_Symbol = TTR Transthyretin precursor |
| | Gene_Symbol = APOB Apolipoprotein B-100 precursor |
| | Gene_Symbol = HP HP Haptoglobin protein |
| Cell proteins | Gene_Symbol = DSP Isoform DPI of Desmoplakin |
| Plasma proteins | Gene_Symbol = TF Serotransferrin precursor |
| | Gene_Symbol = ALB Isoform 2 of Serum albumin precursor |
| | Gene_Symbol = A2M Alpha-2-macroglobulin precursor |
| | Gene_Symbol = IGHA1 IGHA1 protein |

TABLE 3-continued

| Group | Proteins detected |
|---|---|
| | Deep myopia patient 3 |
| Deep myopia relevant proteins | Gene_Symbol = HPX Hemopexin precursor<br>Gene_Symbol = HP Haptoglobin precursor<br>Gene_Symbol = APOB Apolipoprotein B-100 precursor<br>Gene_Symbol = TTR Transthyretin precursor |
| Plasma proteins | Gene_Symbol = TF Serotransferrin precursor<br>Gene_Symbol = FGA Isoform 1 of Fibrinogen alpha chain precursor<br>Gene_Symbol = ALB Uncharacterized protein ALB<br>Gene_Symbol = A2M Alpha-2-macroglobulin precursor<br>Gene_Symbol = IGKV1-5 IGKV1-5 protein<br>Gene_Symbol = IGKC IGKC protein<br>Gene_Symbol = IGL@ IGL@ protein<br>Gene_Symbol = IGHG1 Putative uncharacterized protein DKFZp686N02209<br>Gene_Symbol = IGHA1 IGHA1 protein<br>Gene_Symbol = IGHM FLJ00385 protein (Fragment)<br>Gene_Symbol = -Putative uncharacterized protein DKFZp686K04218 (Fragment)<br>Gene_Symbol = PPBP Platelet basic protein precursor<br>Gene_Symbol = HBB Hemoglobin subunit beta<br>Gene_Symbol = HBG1 Hemoglobin subunit gamma-1<br>Gene_Symbol = CA1 Carbonic anhydrase 1 |
| | Deep myopia patient 4 |
| Deep myopia relevant proteins | Gene_Symbol = HPX Hemopexin precursor<br>Gene_Symbol = HP Haptoglobin precursor<br>Gene_Symbol = APOB Apolipoprotein B-100 precursor<br>Gene_Symbol = TTR Transthyretin precursor |
| Cell proteins | Gene_Symbol = GSN Isoform 1 of Gelsolin precursor<br>Gene_Symbol = POTE2 protein expressed in prostate, ovary, testis, and placenta 2<br>Gene_Symbol = TTN Isoform 2 of Titin |
| Plasma proteins | Gene_Symbol = TF Serotransferrin precursor<br>Gene_Symbol = FGG Isoform Gamma-B of Fibrinogen gamma chain precursor<br>Gene_Symbol = ALB Uncharacterized protein ALB<br>Gene_Symbol = A2M Alpha-2-macroglobulin precursor<br>Gene_Symbol = IGKC IGKC protein<br>Gene_Symbol = IGHM IGHM protein<br>Gene_Symbol = IGKC IGKC protein<br>Gene_Symbol = IGL@ IGL@ protein<br>Gene_Symbol = IGHA1 IGHA1 protein<br>Gene_Symbol = IGL@ IGL@ protein<br>Gene_Symbol = IGHM FLJ00385 protein (Fragment)<br>Gene_Symbol = -Putative uncharacterized protein DKFZp686M24218<br>Gene_Symbol = IGHG1 Putative uncharacterized protein DKFZp686N02209<br>Gene_Symbol = CSTA Cystatin-A<br>Gene_Symbol = HBB Hemoglobin subunit beta<br>Gene_Symbol = APOE Apolipoprotein E precursor<br>Gene_Symbol = TPI1 Isoform 2 of Triosephosphate isomerase |
| | Deep myopia patient 5 |
| Deep myopia relevant proteins | Gene_Symbol = HPX Hemopexin precursor<br>Gene_Symbol = TTR Transthyretin precursor<br>Gene_Symbol = HPR Isoform 1 of Haptoglobin-related protein precursor |
| Plasma proteins | Gene_Symbol = TF Serotransferrin precursor<br>Gene_Symbol = A2M Alpha-2-macroglobulin precursor<br>Gene_Symbol = ALB Uncharacterized protein ALB<br>Gene_Symbol = IGKC IGKC protein<br>Gene_Symbol = IGL@ IGL@ protein<br>Gene_Symbol = IGHA1 CDNA FLJ14473 fis, clone MAMMA1001080, highly similar to *Homo sapiens* SNC73 protein (SNC73) mRNA |
| | Deep myopia patient 6 |
| Deep myopia relevant proteins | Gene_Symbol = TXN Thioredoxin<br>Gene_Symbol = HPX Hemopexin precursor<br>Gene_Symbol = HPR Isoform 1 of Haptoglobin-related protein precursor |

TABLE 3-continued

| Group | Proteins detected |
|---|---|
| Plasma proteins | Gene_Symbol = TF Serotransferrin precursor<br>Gene_Symbol = A2M Alpha-2-macroglobulin precursor<br>Gene_Symbol = IGHG1 Putative uncharacterized protein DKFZp686N02209<br>Gene_Symbol = IGHA1 IGHA1 protein |
| | Deep myopia patient 7 |
| Deep myopia relevant proteins<br>Plasma proteins | Gene_Symbol = HPX Hemopexin precursor<br>Gene_Symbol = APOB Apolipoprotein B-100 precursor<br>Gene_Symbol = TTR Transthyretin precursor<br>Gene_Symbol = TF Serotransferrin precursor<br>Gene_Symbol = A2M Alpha-2-macroglobulin precursor<br>Gene_Symbol = FGA Isoform 1 of Fibrinogen alpha chain precursor<br>Gene_Symbol = ALB Uncharacterized protein ALB<br>Gene_Symbol = IGKV3-20 Ig kappa chain V-III region HAH precursor<br>Gene_Symbol = IGKV1-5 IGKV1-5 protein<br>Gene_Symbol = IGKC IGKC protein<br>Gene_Symbol = IGKV1-5 IGKV1-5 protein<br>Gene_Symbol = IGL@ IGL@ protein<br>Gene_Symbol = IGHA1 IGHA1 protein<br>Gene_Symbol = IGHG2 Putative uncharacterized protein DKFZp686I04196 (Fragment)<br>Gene_Symbol = IGHM IGHM protein<br>Gene_Symbol = CSTA Cystatin-A |
| | Deep myopia patient 8 |
| Deep myopia relevant proteins<br><br>Cell proteins<br><br>Plasma proteins | Gene_Symbol = HPX Hemopexin precursor<br>Gene_Symbol = APOB Apolipoprotein B-100 precursor<br>Gene_Symbol = HP Haptoglobin precursor<br>Gene_Symbol = APOE Apolipoprotein E precursor<br>Gene_Symbol = PDE4A Isoform 3 of cAMP-specific 3',5'-cyclic phosphodiesterase 4A<br>Gene_Symbol = GSN Isoform 1 of Gelsolin precursor<br>Gene_Symbol = ALB Uncharacterized protein ALB<br>Gene_Symbol = TF Serotransferrin precursor<br>Gene_Symbol = A2M Alpha-2-macroglobulin precursor<br>Gene_Symbol = FGA Isoform 1 of Fibrinogen alpha chain precursor<br>Gene_Symbol = FGB Fibrinogen beta chain precursor<br>Gene_Symbol = FGG Isoform Gamma-B of Fibrinogen gamma chain precursor<br>Gene_Symbol = IGKV1-5 IGKV1-5 protein<br>Gene_Symbol = IGKC IGKC protein<br>Gene_Symbol = IGHG1 Putative uncharacterized protein DKFZp686N02209<br>Gene_Symbol = IGHA1 SNC66 protein<br>Gene_Symbol = IGHM FLJ00385 protein (Fragment)<br>Gene_Symbol = IGHM IGHM protein<br>Gene_Symbol = IGL@ IGL@ protein<br>Gene_Symbol = -Putative uncharacterized protein DKFZp686K04218 (Fragment)<br>Gene_Symbol = IGHA1 IGHA1 protein<br>Gene_Symbol = IGL@ IGL@ protein<br>Gene_Symbol = IGHG2 Putative uncharacterized protein DKFZp686I04196 (Fragment)<br>Gene_Symbol = -Ig heavy chain V-III region HIL<br>Gene_Symbol = -Single-chain Fv (Fragment)<br>Gene_Symbol = -Anti-(ED-B) scFV (Fragment) |

Example 5

Detection of Differential Polypeptides of Plasma from Healthy Pregnant Female Volunteers Differential polypeptides preparation: 20 µl plasma collected from healthy pregnant female volunteers were diluted with 980 µl Phosphate buffer (10 mM, pH 7.0) to a total protein about 1 mg. The diluted plasma was loaded onto the affinity column (1 ml) with immobilized affinity media of Example 1. The flow-through was collected and concentrated to 20 µl, while 5 µl was analyzed with reducing SDS-PAGE (12%) and silver stain protocol. It was shown that there were few faint bands visible, confirming the effectiveness of removal of most of the proteins of normal function in healthy human plasma.

Five microliters of the above flow-through proteins were reduced with 100 µl of reducing buffer (200 µl of TCEP in 2 ml Digestion buffer) and incubated at 60° C. for 10 minutes. One hundred microliters of alkylation buffer (60 mg of iodoacetamide (IAA) in 3 ml Digestion buffer) was added to the tube and incubated in the dark at room temperature for 1 hour. Then 20 µl activated Trypsin solution was added to the tube and incubated at 37° C. for 1 hour, followed by continuous incubation at 25° C. overnight with gentle mixing.

Then the peptides mixture was injected onto a Zorbax 300 SB-C18 peptide traps (Agilent Technologies, Wilmington, Del.) to desalt. The separation was performed on a Zorbax 300SB-C18 reverse phase capillary column (150 μm inner diameter×15 cm, Agilent Technologies) at 250 nl/min with a linear gradient of 4-50% B over 50 min (A: 0.1% formic acid; B: 84% CH3CN and 0.1% formic acid), a step up to 100% B in 4 min, and then holding at 100% B for 10 min. The peak was online injected into a Finnigan LTQ (single linear quadrupole ion trap) mass spectrometer for peptide identification.

Mass spectrometry was carried out on a Finnigan LTQ linear ion trap. The MS method consisted of a cycle combining one full MS scan with ten MS/MS events (25% collision energy). Dynamic exclusion duration was set to 30 seconds. The MS/MS spectra from all the runs were searched using BOWORKS protein identification software against database of ipi HUMAN v3.36. The SEQUEST filter was set to when Charge +1, Xcorr≧1.9; Charge +2, Xcorr≧2.2; Charge +3, Xcorr≧3.75; and DelCN≧0.1.

Plasmas collected from healthy pregnant female volunteers were tested. The detected differential proteins/peptides were 8 and 12. The leftover of normal plasma proteins/peptides includes immunoglobulin, transferrin and serine protease inhibitor.

There are some pregnant related proteins detected:

APOB (Apolipoprotein B-100) belongs to plasma protein family. However it was not detected in non-pregnant healthy volunteers. It is reported that the APOB level is raised in intrahepatic cholestasis of pregnancy (ICP). The detection of APOB in the plasma of one of the pregnant healthy volunteers suggested that this volunteer should have a thorough examination for secure the healthy both the mother and fetus.

Hemopexin (HPX) is a low abundant plasma protein with the highest binding affinity to heme among known proteins. Plasma hemopexin activity, associated with increased vascular permeability. It is reported that its abundant level is higher in pregnant healthy volunteer than non-pregnant healthy volunteer.

Sex hormone-binding globulin precursor (SHBG) is another low abundant plasma protein. It is reported that its abundant level increases as the progress of pregnancy, up to as high as 12 fold of non-pregnant healthy volunteer. It is not detected in healthy volunteers in Example 2.

Complement factor B (BF) is a relatively high abundant plasma protein. It is reported apparently high before birth.

The detection of the pregnancy related proteins in plasma is another confirmation of the effectiveness of the differential protein detection process.

In Table 4, the differential proteins/peptides detected from plasma of pregnant woman volunteers, initial classification and comments are shown.

TABLE 4

| Group | Protein name |
|---|---|
| Pregnant female volunteer 1 | |
| Plasma proteins | Gene__Symbol = TF Serotransferrin precursor |
| | Gene__Symbol = IGHM FLJ00385 protein (Fragment) |
| | Gene__Symbol = IGHG2 Putative uncharacterized protein DKFZp686I04196 (Fragment) |
| | Gene__Symbol = IGHG1 Putative uncharacterized protein DKFZp686N02209 |
| | Gene__Symbol = IGKV1-5 IGKV1-5 protein |
| Cell proteins | Gene__Symbol = C1orf131 Isoform 2 of Uncharacterized protein C1orf131 |
| Pregnancy related proteins | Gene__Symbol = CFB Isoform 1 of Complement factor B precursor (Fragment) |
| | Gene__Symbol = HPX Hemopexin precursor |
| Pregnant female volunteer 2 | |
| Plasma proteins | Gene__Symbol = TF Serotransferrin precursor |
| | Gene__Symbol = IGHG2 Putative uncharacterized protein DKFZp686I04196 (Fragment) |
| | Gene__Symbol = IGHM IGHM protein |
| | Gene__Symbol = IGHM FLJ00385 protein (Fragment) |
| | Gene__Symbol = IGKV1-5 IGKV1-5 protein |
| | Gene__Symbol = FETUB Uncharacterized protein FETUB |
| | Gene__Symbol = SERPINA5 Plasma serine protease inhibitor precursor |
| Cell proteins | Gene__Symbol = TTN Isoform 2 of Titin |
| Pregnancy related proteins | Gene__Symbol = HPX Hemopexin precursor |
| | Gene__Symbol = SHBG Isoform 1 of Sex hormone-binding globulin precursor |
| | Gene__Symbol = APOB Apolipoprotein B-100 precursor |
| | Gene__Symbol = CFB Isoform 1 of Complement factor B precursor (Fragment) |

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A process for increasing the concentration of at least one protein or peptide in a biological test sample, wherein the protein or peptide is differentially present in the biological test sample compared to a biological control sample, comprising:

(a) extracting one or more soluble proteins or peptides from the biological control sample, and developing a composition of antigen binding immunoglobulins capable of binding at least one polypeptide in the biological control sample;
(b) immobilizing the immunoglobulins onto a base matrix to prepare an affinity media;
(c) extracting soluble proteins or peptides from a biological test sample; and
(d) passing extracted soluble proteins from the biological test sample through a column packed with the affinity media, collecting the flow-through fraction and concentrating the proteins contained therein, wherein the differential proteins or peptides are enriched in the sample of interest.

2. The process of claim 1, further comprising:
(e) characterizing the enriched polypeptide(s) in the biological test sample.

3. The process of claim 2, wherein the enriched polypeptide(s) is characterized by mass spectrometry.

4. A process for identifying differential protein(s) or peptide(s) between a biological test sample and a biological control sample, wherein said process comprises:
(a) extracting one or more soluble proteins or peptides from the biological control sample, and immunizing an animal with the proteins or peptides to prepare antigen binding proteins capable of binding the soluble proteins or peptides;
(b) immobilizing the antigen binding proteins onto a base matrix to prepare an affinity media;
(c) extracting soluble proteins or peptides from a biological test sample;
(d) passing extracted soluble proteins from the biological test sample through a column packed with the affinity media, collecting the flow-through fraction and concentrating the proteins contained therein, wherein said differential proteins or peptides are enriched in the sample of interest; and
(e) detecting the differential proteins or peptides with mass spectrometry.

5. A process for identifying differential protein(s) or peptide(s) between a biological test sample and a biological control sample, wherein said process comprises:
(a) extracting one or more soluble proteins or peptides from the biological control sample, and immunizing an animal with the proteins or peptides to prepare antigen binding proteins capable of binding the soluble proteins or peptides;
(b) immobilizing the immunoglobulins onto a base matrix to prepare an affinity media;
(c) extracting soluble proteins or peptides from a biological test sample;
(d) mixing the soluble protein extract from the biological test sample with the affinity media, separating and collecting the supernatant fraction and concentrating the proteins contained therein, wherein the differential proteins or peptides are enriched in the sample of interest; and
(e) detecting the differential proteins or peptides with mass spectrometry.

6. The process of claim 1, wherein the antigen binding polypeptides are antibodies or antibody fragments, or combinations thereof.

7. The process of claim 5, wherein the supernatant is collected from the solid affinity media with centrifugation.

8. The process of claim 5, wherein the supernatant is collected from the solid affinity media with a magnetic field.

9. The process of claim 5, wherein the supernatant is collected from the solid affinity media with suction under vacuum.

10. The process of claim 5, wherein the supernatant is collected from the solid affinity media with pressure liquid through solid media.

11. A process of identifying at least one polypeptide as a disease marker in a biological test sample from a subject suffering from said disease, wherein said polypeptide(s) is differentially present in the biological test sample compared to a biological control sample from another subject free of said disease, comprising:
(a) extracting soluble polypeptides from said biological control sample;
(b) developing antigen binding polypeptides capable of binding to said extracted soluble polypeptides;
(c) immobilizing said antigen binding polypeptides onto a base matrix to prepare an affinity media;
(d) extracting soluble polypeptides from said biological test sample;
(e) passing extracted soluble proteins in (d) through a column packed with the affinity media and collecting the flow-through fraction, such that the concentration percentage of said polypeptide(s) as the disease marker to the total polypeptides in the biological test sample in said flow-through fraction is increased;
(f) optionally, concentrating said polypeptide(s) in the flow-through fraction; and
(g) identifying the polypeptide(s) as the disease marker.

12. The process of claim 11, wherein the identified disease marker can be further used for diagnostic or therapeutic purpose.

13. The process of claim 11, wherein both subjects are humans.

14. The process of claim 1, wherein the biological sample is a biological sample selected from a patient group, wherein the patient suffers from arthritis, autoimmune disease, bacterial infection, blood disorder, cancer, cardiovascular disease, diabetes, genetic disorder, inflammation, mental disease, metabolic disorder, neurological disorders, respiratory diseases and viral infection.

15. The process of claim 14, wherein the cancer patient suffers from adrenal cancer, bile duct cancer, extrahepatic bile duct cancer, bladder cancer, bone cancer, brain cancer, breast cancer, cervical cancer, colon cancer, colorectal cancer, esophageal cancer, gallbladder cancer, gastric cancer, head & neck cancer, Hodgkin's disease, lymphoma, intestinal cancer, kidney cancer, laryngeal cancer, leukemia, acute lymphocytic leukemia (all), acute myelogenous leukemia (aml), chronic lymphocytic leukemia (cll), liver cancer, lung cancer, also see small cell, non-small cell, lymphoma, b-cell lymphoma, melanoma, mesothelioma, multiple myeloma, oral cancer, ovarian cancer, pancreatic cancer, pharyngeal cancer, prostate cancer, rectal cancer, rectum cancer, skin cancer, stomach cancer, testicular cancer, throat cancer, thyroid cancer, uterine cancer, vaginal cancer, or vulvar cancer.

16. The process of claim 14, wherein the neurological disorder is Alzheimer's disease, Parkinson's disease, dementia, epilepsy, headache disorders, multiple sclerosis, neuroinfections, stroke or traumatic brain injuries.

17. The process of claim 1, wherein the biological sample is body fluid selected from the group consisting of ascites, blood, plasma, serum, chyle, semen, interstitial fluid, lymph fluid, menses, breast milk, sweat, tears, urine, vaginal lubrication, Cowper's fluid or pre-ejaculatory fluid, female ejaculate, mucus, pleural fluid, pus, saliva, sebum (skin oil), chyme, and vomit.

18. The process of claim 1, wherein the biological sample is a patient body tissue selected from aorta, artery, bladder, bone, breast, cervix, colon, esophagus, fungi, kidney, liver, lung, pancreas, placenta, skin, small intestine, spinal cord, spleen, stomach, thyroid, tonsil, or uterus.

19. The process of claim 1, wherein the biological sample is from mice, rats, pigs, guinea pigs, rabbits, horses, cows, dogs, cats, monkeys and humans.

20. The process of claim 1, wherein the process is used to screen disease biomarkers from plasma.

21. The process of claim 1, wherein the process is used to screen disease biomarkers from pathologic tissue.

22. The process of claim 1, wherein the process is used to assess health risks for individuals.

23. The process of claim 1, wherein the process is used to discover drug targets.

24. The process of claim 1, wherein the process is used to monitor the therapeutic effect of disease treatment.

25. The process of claim 1, wherein the process is used for personalized treatment for diseases.

26. The process of claim 1, wherein the process is used to identify a treatment regimen.

27. The process of claim 11, wherein the putative uncharacterized protein DKFZp686O01196 is identified as a disease marker from liver cancer patients.

28. The process of claim 11, wherein HPX (Hemopexin), Transthyretin or Isoform 1 of Haptoglobin-related protein is identified as a disease marker from myopia patients.

29. A process for increasing the concentration of at least one protein or polypeptide in a biological test sample, wherein the protein(s) or polypeptide(s) is differentially present in the biological test sample compared to a biological control sample, comprising:

(a) extracting one or more soluble proteins or peptides from the biological control sample, and developing a composition of antigen binding immunoglobulins capable of binding at least one polypeptide in the biological control sample;

(b) immobilizing the immunoglobulins onto a base matrix to prepare an affinity media;

(c) extracting soluble proteins or peptides from the biological test sample; and (d) contacting the soluble proteins from the biological test sample with the affinity media, and collecting a resulting sample, wherein the differential proteins or peptides are enriched in the resulting sample.

* * * * *